United States Patent [19]

Barrett et al.

[11] Patent Number: 5,683,983
[45] Date of Patent: Nov. 4, 1997

[54] PEPTIDES AND COMPOUNDS THAT BIND TO THE IL-5 RECEPTOR

[75] Inventors: Ronald W. Barrett, Sunnyvale; Bruce P. England, Fremont; Peter J. Schatz, Mountain View; Derek Sloan, Los Gatos; Min-Jia Chen, San Francisco, all of Calif.

[73] Assignee: Glaxo Group Limited, Greenford, England

[21] Appl. No.: 484,083

[22] Filed: Jun. 7, 1995

[51] Int. Cl.$^6$ .................. A61K 38/00; A61K 38/21; C07K 10/00; C12P 21/08
[52] U.S. Cl. .................................................. 514/12
[58] Field of Search ........................ 514/12; 424/85.8; 530/387–388

[56] References Cited

U.S. PATENT DOCUMENTS

| | | | |
|---|---|---|---|
| 5,096,704 | 3/1992 | Coffman et al. | 424/85.8 |
| 5,143,854 | 9/1992 | Pirrung et al. | 436/518 |
| 5,270,170 | 12/1993 | Schatz et al. | 435/7.37 |
| 5,338,665 | 8/1994 | Schatz et al. | 435/6 |

FOREIGN PATENT DOCUMENTS

| | | |
|---|---|---|
| 2058003 | 6/1992 | Canada . |
| 2078384 | 3/1993 | Canada . |
| 0 475 746 A1 | 9/1991 | European Pat. Off. . |
| 0 533 006 A1 | 9/1992 | European Pat. Off. . |
| WO 90/15070 | 12/1990 | WIPO . |
| WO 93/16184 | 8/1993 | WIPO . |
| WO 94/28170 | 12/1994 | WIPO . |
| WO 95/14040 | 5/1995 | WIPO . |

OTHER PUBLICATIONS

Barker et al., (1992) *J. Med. Chem.* 35:2040–2048 Cyclic RGD peptide analogues as antiplatelet antithrombotics.
Bodanszky et al., (1966) *Chem. Ind.* (London) 38:1597–1598 Active esters and resins in peptide synthesis.
Caras et al., (1989) *Science* 243:1196–1198 Signal peptide for protein secretion directing glycophospholipid membrane anchor attachment.
Chiu et al., (1984) *Archives Internationales de Pharmacodynamie et de Therapie* 270:128–140 Gastric cytoprotective properties of SCH 32651, a novel antiulcer agent.
Cwirla et al., (1990) *Proc. Natl. Acad. Sci. USA* 87:6378–6382 Peptides on phage: A vast library of peptides for identfying ligands.
Dower et al., (1988) *Nucleic Acids Research* 16:6127–6145 High efficiency transformation of *E. coli* by high voltage electroporation.

Dower et al., (1991) *Ann. Rep. Med. Chem.* 26:271–280 Recombinant and synthetic randomized peptide libraries.
Fodor et al., (1991) *Science* 251:767–773 Light–directed, spatially addressable parallel chemical synthesis.
Hayashida et al., (1990) *Proc. Natl. Acad. Sci. USA* 87:9655–9659 Molecular cloning of a second subunit of the receptor for human granulocyte–macrophage colony–stimulating factor (GM–CSF): Reconstitution of a high–affinity GM–CSF receptor.
Lin et al., (190) *Science* 249:677–679 Expression of T cell antigen receptor heterodimers in a lipid–linked form.
Lopez et al., (1988) *J. Exp. Med.* 167:219–224 Recombinant human interleukin 5 is a selective activator of human eosinophil function.
Murata (1992) *J. Exp. Med.* 175:341–351 *Molecular cloning and expression of the human interleukin 5 receptor.*
Or et al., (1991) *J. Org. Chem.* 56: 3146–3149 Cysteine alkylation in unprotected peptides: synthesis of a carbavasopressin analogue by intramolecular cysteine alkylation.
Plaetinick et al., (1990) *J. Exp. Med.* 172:683–691 Characterization of interleukin 5 receptors on eosinophilic sublines from human promyelocytic leukemia (HL–60) cells.
Raeburn et al., (1992) *J. Pharmocol. Toxicol. Meth.* 27:143–159 Techniques for drug delivery to the airways and the assessment of lung function in animal models.
Rizo et al., (1992) *Annu. Rev. Biochem.* 61:387–418 Constrained peptides: Model of Bioactive peptides and protein substructures.
Rolink et al., (1989) *J. Exp. Med.* 169:1693–1701 Monoclonal antibodies reactive with the mouse interleukin 5 receptor.
Saito et al., (1988) *Proc. Natl. Acad. Sci. USA* 85:2288–2292 Selective differentiation and proliferation of hematopoietic cells induced by recombinant human interleukins.
Wanner et al., (1990) *Am. Rev. Respir. Dis.* 141:253–257 Models of airway hyperresponsiveness.
Yamaguchi et al., (1988) *J. Exp. Med.* 167:43–56 Purified interleukin 5 supports the terminal differentiation and proliferation of murine eosinophilic precursors.

*Primary Examiner*—Cecilia J. Tsang
*Assistant Examiner*—Jennifer Harle
*Attorney, Agent, or Firm*—Lauren L. Stevens

[57] ABSTRACT

Described are peptides and peptide mimetics that bind to and the IL-5 receptor. Such peptides and peptide mimetics are useful in methods for treating disorders that involve improper production of or response to IL-5 and or the production and accumulation of eosinophils, such as asthma, as well as in diagnostic methods employing labeled peptides and peptide mimetics.

15 Claims, 5 Drawing Sheets

Fig. 1b
pJS142 Library Vector, cloning sites at 3' end of lacI gene:

```
---lacI------><-----------------linker---------------->.
                          Sfi I           Eag I
              Xho I       Stu I    Hpa I  Sfi I    Msc I     Sal I
              L  E  S  G  Q  V  V  H  G  E  Q  V  G  G  E  A  S  G  A  V  N  G  R  G  L  A  G  Q  *    (SEQ ID NO: 51)
              CTCGAGAGCGGGCAGgtgtgcatgggagcaggtggtgggtggtgagGCCTCCGGGGCCCGTGGCCCGTTAACGGCCGTGGCCTAGCTGGCCAATAAGtcgac
              GAGCTCTCGCCCGTCcaccacgtacccctcgtccaccactcCGGAGGCCCCGGGCACCGGGCAATTGCCGGCACCGGATCGACCGGTTATTcagctg    (SEQ ID NO: 52)
```

Fig. 1c
Library Construction after SfiI digestion:

```
---lacI------><-----------------linker----------------><library>                                (SEQ ID NO: 53)
                          BspE I
              Xho I       Stu I                                                          Msc I     Sal I
              L  E  S  G  Q  V  V  H  G  E  Q  V  G  G  E  A  S  G  G  G   Xn   *
              CTCGAGAGCGGGCAGgtgtgcatgggagcaggtggtgggtggtgagGCCTCCG gaggtggt (NNK)n taactaagtaaagc TGGCCAATAAgtcgac
              GAGCTCTCGCCCGTCcaccacgtacccctcgtccaccactcCGGA ggcctccacca          attgattcatt TCGACCGGTTATTcagctg
```

Fig. 2a
pELM3/pELM15 MBP vector cloning sites:

```
---MBP---->  <----------------------linker----------------------->  <-----Xa
  Q   T   N   S   S   S   N   N   N   N   N   N   N   N   N   L   G   I   E
 CAG ACT AAT TCG AGC TCG AAC AAC AAT AAC AAC AAC AAC AAC CTC GGG ATC GAG
 GTC TGA TTA AGC TCG AGC TTG TTG TTA TTG TTG TTG TTG TTG GAG CCC TAG CTC
                                                                                (SEQ ID NO: 54)
                                                                                (SEQ ID NO: 55)

Xa---->  <-----------------------cloning sites------------------------->
         Age I  Pml I  Sma I  EcoR I  BamH I  Xba I  Sal I  Pst I    Hind III
   G   R   T   G   H   V   A   R   E   F   G   S   S   R   V   D   L   Q   A   S
  GGA AGG ACC GGT CAC GTG GCC CGG GAA TTC GGA TCC TCT AGA GTC GAC CTG CAG GCA AGC TT
  CCT TCC TGG CCA GTG CAC CGG GCC CTT AAG CCT AGG AGA TCT CAG CTG GAC GTC CGT TCG AA
```

Fig. 2b
pELM3/pELM15 after subcloning of library insert:

```
                                                                                (SEQ ID NO: 56)

Xa---->  <----linker---->  <library>                            Msc I        Sal I
   G   R   T   G   G   G   Xn    *
  GGA AGG ACC GGA GGT GGT (NNK)n  TAA CTA AGT AAA GCT GGC CAA TAA GTC GAC
  CCT TCC TGG CCT CCA CCA (NNM)n  ATT GAT TCA TTT CGA CCG GTT ATT CAG CTG
```

Fig. 3b
pCMG14 Library Vector, cloning sites at 3' end of Headpiece Dimer gene:

```
-------Headpiece----------><----linker----->
                                    Sfi I                              Eag I
                      Stu I         Hpa I   Sfi I    Msc I      Sal I
  E  A  M  A  E  L  N  Y  I  P  R  S  Q  E  A  S  G  A  V  N  G  R  G  L  A  G  Q  *          (SEQ ID NO: 57)
GAAGCGGGCGATGGCGGAGCTGAATTACATTCCCcggtcgcaggagGCCTCCGGGGCCGTGAACGGCCGTTAACGGCCTAGCTGGCCAATAAgtcgac
CTTCGCCCGCTACCGCCTCGACTTAATGTAAGGGgccagcgtcctcCGGAGGCCCCGGCACGTTGCCGGCAATTGCCGGATCGACCGGTTATTcagctg                (SEQ ID NO: 58)
```

Fig. 3c
Library Construction after SfiI digestion:

```
--------Headpiece-----------><-----linker---------><library>
                                                                                       ON-1679
 Xho I                         Stu I        BspE I                           (SEQ ID NO: 59)     Msc I    Sal I
  E  A  M  A  E  L  N  Y  I  P  R  S  Q  E  A  S  G  G  G      X12             *
GAAGCGGGCGATGGCGGAGCTGAATTACATTCCCcggtcgcaggagGCCTCCGGAggcctccacca        gaggtggt (NNK) 12   taactaagtaaagc TGGCCAATAAgtcgac
CTTCGCCCGCTACCGCCTCGACTTAATGTAAGGGgccagcgtcctcCGGA ggcctccacca                                attgattcatt TCGACCGGTTATTcagctg
                                                          ↑                                             ↑
                                                       ON-829                                        ON-830
```

PEPTIDES AND COMPOUNDS THAT BIND TO THE IL-5 RECEPTOR

CROSS-REFERENCE TO RELATED CASES

This application is related to the subject matter of U.S. patent application Ser. Nos. 08/478312, 08/485302 and 08/476169, each of which is filed simultaneous herewith and is entitled "PEPTIDES AND COMPOUNDS THAT BIND TO THE IL-5 RECEPTOR", and each of which is expressly incorporated herein by reference.

BACKGROUND OF THE INVENTION

The present invention provides peptides and compounds that bind the interleukin 5 receptors (IL-5R), methods for assaying interleukin 5 (IL-5), and methods for inhibiting the binding of IL-5 to the IL-5R. The invention has application in the fields of biochemistry and medicinal chemistry and particularly provides IL-5 antagonists for use in the treatment of human disease.

Interleukin-5 (IL-5 or IL5) is a lymphokine secreted by T cells and mast cells having biological activities on B cells and eosinophils. In murine hematopoiesis, IL-5 is a selective signal for the proliferation and differentiation of the eosinophilic lineage. See Yamaguchi et al. (1988) *J. Exp. Med.* 167:43–56. In this respect, IL-5 function shows analogies with colony-stimulating factors for other myeloid lineages. Also, human (h) IL-5 is very potent in the activation of human eosinophils. See Lopez et al. (1988) *J. Exp. Med.* 167:219–224 and Saito et al. (1988) *Proc. Natl. Acad. Sci. USA* 85:2288–2292.

IL-5 mediates its activity through a cell membrane receptor-complex. This complex has been characterized physicochemically in both the murine and human system. Mouse pre-B cell lines depending on IL-5 for their growth have been developed from bone marrow and are used for IL-5 receptor analysis. See Rolink et al. (1989) *J. Exp. Med.* 169:1693–1701. The human IL-5 receptor can be studied on a subclone of the promyelocytic cell line HL60 induced towards eosinophil differentiation. See Plaetinck et al. (1990) *J. Exp. Med.* 172:683–691.

Eosinophilic differentiation is initiated using sodium butyrate. Only high affinity (Kd=30 pM) IL-5 binding sites can be found on these cells. However, cross-linking studies reveal the presence of two polypeptide chains involved in IL-5 binding, i.e., IL-5R-$\alpha$ and IL-5R-$\beta$ chains. Devos et al. Canadian Patent Publication 2,058,003 describes a recombinant $\alpha$ chain of human IL-5R or parts thereof, DNA-sequences coding for such a receptor or parts thereof, and host cells transformed with such vectors. Takatsu et al. European Patent Publication 475,746 provides an isolated cDNA sequence coding for murine and human IL-5 receptor.

A soluble human IL-5R-$\alpha$ chain can be used as an IL-5 antagonist in chronic asthma or other disease states with demonstrated eosinophilia. Eosinophils are white blood cells of the granulocytic lineage. Their normal function appears to be combating parasitic infections, particularly helminthis infections. However, their accumulation in tissues, a conditions referred to as eosinophilia, is also associated with several disease states, most notably asthma. It is believed that the damage to the epithelial lining of the bronchial passages in severe asthmatic attacks is largely caused by the compounds released by degranulating eosinophils.

In U.S. Pat. No. 5,096,704, there is specifically disclosed the use of compounds which block the stimulatory effects of IL-5 in order to inhibit production and accumulation of eosinophils. The stimulatory effects of IL-5 were blocked by administering an effective amount of an antagonist to human interleukin-5, preferably using monoclonal antibodies or binding compositions derived therefrom by standard techniques. Monoclonal antibodies were selected by their ability to inhibit IL-5 induced effects in standard IL-5 bioassays, such as the ability to stimulate the growth and development of eosinophils in in vitro colony forming assays, and the ability to augment in vitro proliferation of the in vivo passaged BCL1 lymphoma cells. The use of antibody fragments, e.g., Fab fragments, was also reported.

Currently glucocorticoid steroids are the most effective drugs for treating the acute effects of allergic diseases, such as asthma. However, prolonged steroid treatment is associated with many deleterious side effects. Moreover, the steroids apparently do not affect the production or accumulation of granulocytic cells, such as eosinophils, in the afflicted tissues. The availability of alternative or complementary approaches to the treatment of disorders associated with eosinophilia would have important clinical utility.

The availability of cloned genes for IL-5R, including a soluble IL-5R derivative, facilitates the search for agonists and antagonists of these important receptors. The availability of the recombinant receptor protein allows the study of receptor-ligand interaction in a variety of random and semi-random peptide diversity generation systems. These systems include the "peptides on plasmids" system described in U.S. Pat. No. 5,270,170, the "peptides on phage" system described in U.S. patent application Ser. No. 718,577, filed Jun. 20, 1991, and in Cwirla et al., (1990) *Proc. Natl. Acad. Sci. USA* 87:6378–6382, and the "very large scale immobilized polymer synthesis" system described in U.S. Pat. No. 5,143,854; PCT patent publication No. 90/15070, published Dec. 13, 1990; U.S. patent application Ser. No. 624,120, filed Dec. 6, 1990; Fodor et al., 15 Feb. 1991, *Science* 251:767–773; Dower and Fodor (1991) *Ann. Rep. Med. Chem.* 26:271–180; and U.S. patent application Ser. No. 805,727, filed Dec. 6, 1991; each of the foregoing patent applications and publications is incorporated herein by reference.

Asthma has become the most common chronic disease in industrialized countries. To date, conventional methods and therapeutic agents have not proved to be effective in the treatment of asthma or other immunomediated inflammatory disorders. Moreover, there remains a need for compounds that bind to or otherwise interact with the IL-5R, both for studies of the important biological activities mediated by this receptor and for treatment of disease. The present invention provides such compounds.

SUMMARY OF THE INVENTION

This invention is directed, in part, to the novel and unexpected discovery that defined low molecular weight peptides and peptide mimetics have strong binding properties to the IL-5 R. Accordingly, such peptides and peptide mimetics are useful for therapeutic purposes in treating conditions mediated by IL-5 or involving improper production of or response to IL-5 and can be used to inhibit production and accumulation of eosinophils. These compounds will find particular use in the treatment of asthma. Thus, the present invention also provides a method for treating a patient having a disorder that is susceptible to treatment with a IL-5 inhibitor receives, or is administered, a therapeutically effective dose or amount of a compound of the present invention.

Peptides and peptide mimetics suitable for therapeutic and/or diagnostic purposes have an $IC_{50}$ of about 2 mM or less, as determined by the binding affinity assay set forth in Example 3 below wherein a lower $IC_{50}$ correlates to a stronger binding affinity to IL5-R. For pharmaceutical purposes, the peptides and peptidomimetics preferably have an $IC_{50}$ of no more than about 100 μm. In a preferred embodiment, the molecular weight of the peptide or peptide mimetic is from about 250 to about 5000 daltons.

When used for diagnostic purposes, the peptides and peptide mimetics preferably are labeled with a detectable label and, accordingly, the peptides and peptide mimetics without such a label serve as intermediates in the preparation of labeled peptides and peptide mimetics.

Peptides meeting the defined criteria for molecular weight and binding affinity for IL-5R comprise ten or more amino acids wherein the amino acids are naturally occurring or synthetic (non-naturally occurring) amino acids. Peptide mimetics include peptides having one or more of the following modifications:

peptides wherein one or more of the peptidyl [—C(O) NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl];

peptides wherein the N-terminus is derivatized to a —NRR$^1$ group; to a —NRC(O)R group; to a —NRC(O)OR group; to a —NRS(O)$_2$R group; to a —NHC(O)NHR group where R and R$^1$ are hydrogen or lower alkyl with the proviso that R and R$^1$ are not both hydrogen; to a succinimide group; to a benzyloxycarbonyl—NH—(CBZ—NH—) group; or to a benzyloxycarbonyl—NH— group having from 1 to 3 substituents on the phenyl ring selected from the group consisting of lower alkyl, lower alkoxy, chloro, and bromo; or peptides wherein the C terminus is derivatized to —C(O)R$^2$ where R$^2$ is selected from the group consisting of lower alkoxy, and —NR$^3$R$^4$ where R$^3$ and R$^4$ are independently selected from the group consisting of hydrogen and lower alkyl.

Accordingly, preferred preferred peptides and peptide mimetics comprise a compound having:

(1) a molecular weight of less than about 5000 daltons, and (2) a binding affinity to IL-5R as expressed by an $IC_{50}$ of no more than about 100 μm, wherein from zero to all of the —C(O)NH— linkages of the peptide have been replaced by a linkage selected from the group consisting of a —CH$_2$OC(O)NR— linkage; a phosphonate linkage; a —CH$_2$S(O)$_2$NR— linkage; a —CH$_2$NR— linkage; and a —C(O)NR$^6$— linkage; and a —NHC(O)NH— linkage where R is hydrogen or lower alkyl and R$^6$ is lower alkyl, further wherein the N-terminus of said peptide or peptide mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl-NH— group; and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, and physiologically acceptable salts thereof.

In a related embodiment, the invention is directed to a labeled peptide or peptide mimetic comprising a peptide or peptide mimetic described as above having covalently attached thereto a label capable of detection.

More preferably, these peptides are ten to forty or more amino acid residues in length, preferably ten to twenty-five amino acid residues in length, and comprise a core sequence of amino acids:

$C\ X_1\ X_2\ W\ X_3\ R\ C\ X_4\ X_5\ C$ where $X_1$ is G, I, V, or Y; $X_2$ is D or E; $X_3$ is A or V; $X_4$ is Q or P; and $X_5$ is A, E, K, M, N, S, or T, and dimers and oligomers thereof (SEQ ID NO:1). Preferably, the core peptide comprises a sequence of amino acids:

$C\ X_1\ X_2\ W\ X_3\ R\ C\ X_4\ X_5\ C$ where $X_1$ is V; $X_2$ is E; $X_3$ is A; $X_4$ is P (SEQ ID NO:2). More preferably, the core peptide comprises either a sequence of amino acids:

$X_6\ X_7\ X_8\ V\ C\ X_1\ X_2\ W\ X_3\ R\ C\ X_4\ X_5\ C$ where $X_6$ is D, E, G, I, M, N, P, Q, S, V, or Y; $X_7$ is G, V, or Y; and $X_8$ is F, W, or Y (SEQ ID NO:3); or a sequence of amino acids:

$C\ X_1\ X_2\ W\ X_3\ R\ C\ X_4\ X_5\ C\ X_9$ where $X_9$ is E, I, K, L, M, Q, R, T, V, or Y (SEQ ID NO:4).

Preferably, the core peptide comprises a sequence of amino acids: $X_6\ X_7\ X_8\ V\ C\ X_1\ X_2\ W\ X_3\ R\ C\ X_4\ X_5\ C\ X_9$ (SEQ ID NO:65) More preferably, $X_6$ is D, E, G, N, P, or Q; $X_7$ is G; and $X_{10}$ is K, L, Q, R, or T (SEQ ID NO:5). Most preferably, $X_6$ is D, N, or P; $X_8$ is F or Y; and $X_{10}$ is K, R, or T (SEQ ID NO:6)

Preferred peptides include those listed in the tables above. Particularly preferred peptides include: D G Y V C V E W A R C P T C K (SEQ ID NO:7); D G Y V C V E W A R C P M C T (SEQ ID NO:8); and D G F V C V E W A R C P N C R (SEQ ID NO:9).

The invention also provides for pharmaceutical compositions comprising one or more of the compounds described herein and a physiologically acceptable carrier. These pharmaceutical compositions can be in a variety of forms including oral dosage forms, as well as inhalable powders and solutions and injectable and infusible solutions.

BRIEF DESCRIPTION OF THE FIGURES

FIGS. 1A–C illustrates the construction of peptides-on-plasmids libraries in vector pJS142. FIG. 1A shows a restriction map and position of the genes. The library plasmid includes the rrnB transcriptional terminator, the bla gene to permit selection on ampicillin, the M13 phage intragenic region (M13 IG) to permit rescue of single-stranded DNA, a plasmid replication origin (ori), two lacO$_s$ ssequence, and the araC gene to permit positive and negative regulation of the araB promoter driving expression of the lac fusion gene. FIG. 1B shows the sequence of the cloning region at the 3' end of the lac I gene, including the SfiI and EagI sites used during library construction. FIG. 1C shows the ligation of annealed library oligonucleotides, ON-829 and ON-830, to SfiI sites of pJS142 to produce a library. Singles spaces in the sequence indicate sites of ligation.

FIGS. 2A–B illustrate cloning into the pELM3 and pELM15 MBP vectors. FIG. 2A shows the sequence at the 3' end of the malE fusion gene, including the MBP coding sequence, the poly asparagine linker, the factor Xa protease cleavage site, and the available cloning sites. The remaining portions of the vectors are derived from pMALc2 (pELM3) and pMALp2 (pELM15), available from New England Biolabs. FIG. 2B shows the sequence of the vectors after transfer of the BspEII-ScaI library fragment into AgeI-ScaI digested pELM3/pELM15. The transferred sequence includes the sequence encoding the GGG peptide linker from the pJS142 library.

FIG. 3B depicts the sequence of the cloning region at the 3' end of the headpiece dimer gene, including the SfiI and EagI sites used during library construction. FIG. 3C shows the ligation of annealed ON-1679, ON-829, and ON-830 to SfiI sites of pCMG14 to produce a library. Singles spaces in the sequence indicate sites of ligation.

DESCRIPTION OF SPECIFIC EMBODIMENTS

I. Definitions and General Parameters

Figure 1A:
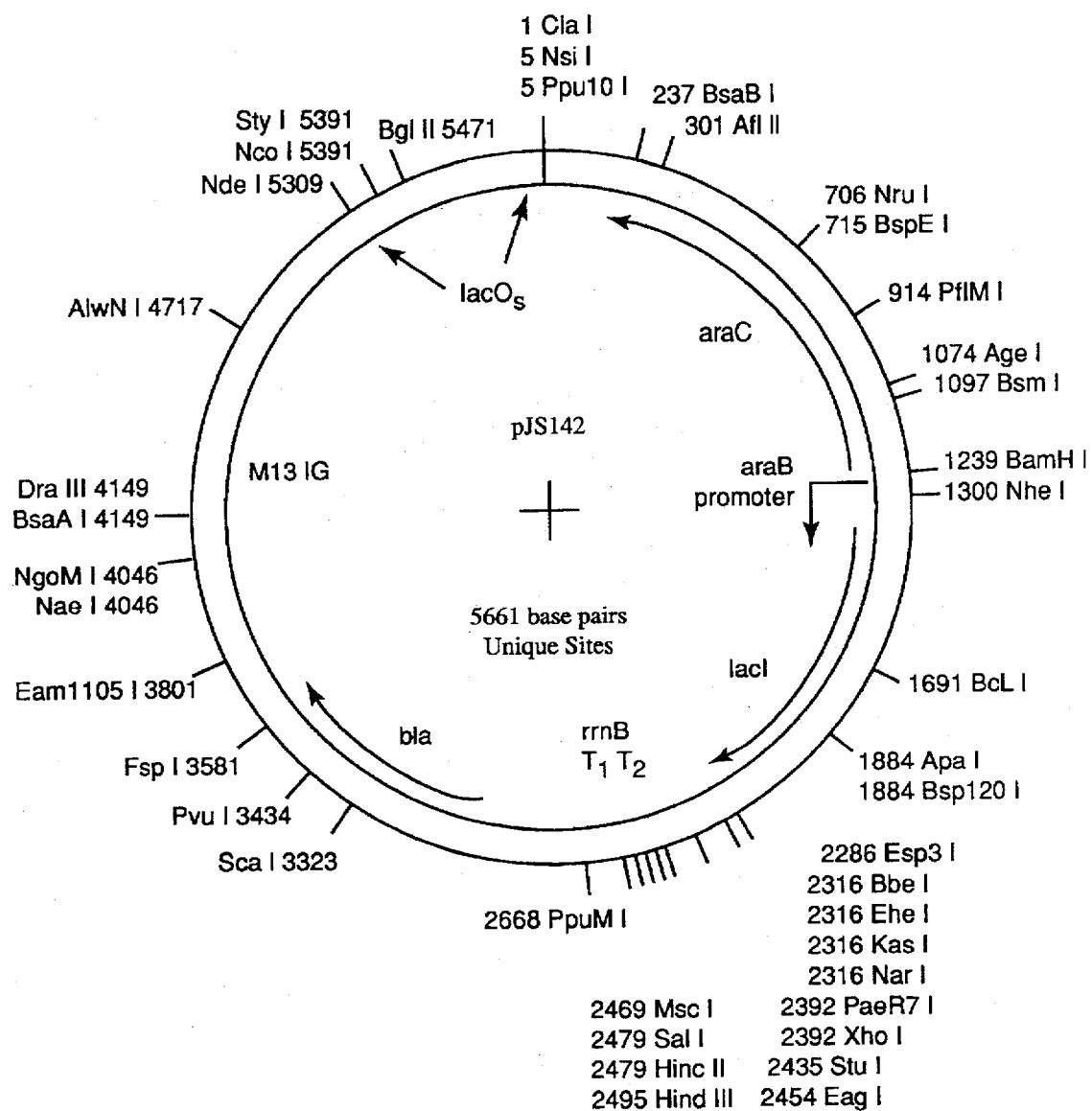

The following definitions are set forth to illustrate and define the meaning and scope of the various terms used to describe the invention herein.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H., supra.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., ed., (1985) *Design of Prodrugs*, Elsevier Science Publishers, Amsterdam. These esters are typically formed from the corresponding carboxylic acid and an alcohol. Generally, ester formation can be accomplished via conventional synthetic techniques. (See, e.g., March *Advanced Organic Chemistry*, 3rd Ed., John Wiley & Sons, New York (1985) p. 1157 and references cited therein, and Mark et al. *Encyclopedia of Chemical Technology*, John Wiley & Sons, New York (1980).) The alcohol component of the ester will generally comprise (i) a $C_2$–$C_{12}$ aliphatic alcohol that can or can not contain one or more double bonds and can or can not contain branched carbon chains or (ii) a $C_7$–$C_{12}$ aromatic or heteroaromatic alcohols. This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H., ed., (1985) *Design of Prodrugs*, Elsevier Science Publishers, Amsterdam. These amides are typically formed from the corresponding carboxylic acid and an amine. Generally, amide formation can be accomplished via conventional synthetic techniques. (See, e.g., March *Advanced Organic Chemistry*, 3rd Ed., John Wiley & Sons, New York (1985) p. 1152 and Mark et al. *Encyclopedia of Chemical Technology*, John Wiley & Sons, New York (1980).) This invention also contemplates the use of those compositions which are both amides as described herein and at the same time are the pharmaceutically acceptable acid addition salts thereof.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve a decrease in the immunological and/or inflammatory responses to infection or tissue injury.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15:29; Veber and Freidinger (1985) TINS p.392; and Evans et al. (1987) J. Med. Chem. 30:1229, which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in CHEMISTRY AND BIOCHEMISTRY OF AMINO ACIDS, PEPTIDES, AND PROTEINS, B. Weinstein, eds., Marcel Dekker, New York, p. 267 (1983); Spatola, A. F., Vega Data (March 1983), Vol. 1, Issue 3, PEPTIDE BACKBONE MODIFICATIONS (general review); Morley, Trends Pharm Sci (1980) pp. 463–468 (general review); Hudson, D. et al., (1979) Int J Pept Prot Res 14:177–185 (—CH$_2$NH—, CH$_2$CH$_2$—); Spatola et al., (1986) Life Sci 38:1243–1249 (—CH$_2$—S); Hann (1982) J. Chem. Soc. Perkin Trans. 1 307–314 (—CH—CH—, cis and trans); Almquist et al., (1980) J Med Chem 23:1392–1398 (—COCH$_2$—); Jennings-White et al., (1982) Tetrahedron Lett 23:2533 (—COCH$_2$—); Szelke et al., (1982) European Appln. EP 45665 CA: 97:39405 (1982) (—CH(OH)CH$_2$—); Holladay et al., (1983) Tetrahedron Lett 24:4401–4404 (—C(OH)CH$_2$—); and Hruby (1982) Life Sci 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Biochem. 61: 387, incorporated herein by reference); for example, by adding internal cysteine residues capable of forming intramolecular disulfide bridges which cyclize the peptide.

II. Overview

The present invention provides compounds that bind to the IL-5R. These compounds include "lead" peptide compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor. The present invention also provides compositions comprising an effective IL-5R binding, IL-5 blocking compound, and more particularly a compound, that is useful for treating disorders associated with the overexpression of IL-5 or with the production and accumulation of eosinophils.

III. Identification of peptides which bind IL-5R

Peptides having a binding affinity to IL-5R can be readily identified by random peptide diversity generating systems coupled with an affinity enrichment process.

Specifically, random peptide diversity generating systems include the "peptides on plasmids" system described in U.S. patent application Ser. No. 07/963,321, filed on Oct. 15, 1992, which is a continuation-in-part application of U.S. patent application Ser. No. 07/778,233, filed on Oct. 16, 1991, (now U.S. Pat. No. 5,270,170) and the "peptides on phage" system described in U.S. patent application Ser. No. 07/718,577, filed on Jun. 20, 1991; and in Cwirla et al. (1990) Proc. Natl. Acad. Sci. USA 87:6378–6382; and No. 07/847,567, filed Mar. 5, 1992; the "encoded synthetic library" (ESL) system described in U.S. patent application Ser. No. 07/946,239, filed Sep. 18, 1992; and the "very large scale immobilized polymer synthesis" (VLSIPS™) system described in U.S. Pat. No. 5,143,854; International Patent Application PCT WO 90/15070; U.S. patent application Ser. No. 07/624,120, filed on Dec. 6, 1990; Fodor et al. (1991) Science 251:767–773; Dower et al. (1991) Ann. Rep. Med. Chem. 26:271–280; and U.S. patent application Ser. No. 07/805,727, filed Dec. 6, 1991, the disclosures of each of which are incorporated herein by reference in their entirety.

Using the procedures described above, random peptides were generally designed to have a defined number of amino acid residues in length (e.g., 12). To generate the collection of oligonucleotides encoding the random peptides, the codon motif (NNK)x, where N is nucleotide A, C, G, or T (equimolar; depending on the methodology employed, other nucleotides can be employed), K is G or T (equimolar), and x is an integer corresponding to the number of amino acids in the peptide (e.g., 12) was used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

In the systems employed, the random peptides were presented either on the surface of a phage particle, as part of a fusion protein comprising either the pIII or the pVIII coat protein of a phage fd derivative (peptides on phage) or as a fusion protein with the LacI peptide fusion protein bound to a plasmid (peptides on plasmids).

The phage or plasmids, including the DNA encoding the peptides, were identified and isolated by an affinity enrichment process using immobilized IL-5R. The affinity enrichment process, sometimes called "panning," involves multiple rounds of incubating the phage or plasmids with the immobilized receptor, collecting the phage or plasmids that bind to the receptor (along with the accompanying DNA), and producing more of the phage or plasmids (along with the accompanying LacI-peptide fusion protein) collected. The extracellular domain (ECD) of the α-chain of the IL-5R, the ECD of the β-chain of the IL-5R, the α-chain of the IL-5R, β-chain of the IL-5R, or the α/β-heterodimer can be used during panning.

After several rounds of affinity enrichment, the phage or plasmids and accompanying peptides were examined by ELISA to determine if the peptides bind specifically to TPO-R. This assay was carried out similarly to the procedures used in the affinity enrichment process, except that after removing unbound phage, the wells were typically treated with rabbit anti-phage antibody, then with alkaline phosphatase (AP)-conjugated goat anti-rabbit antibody. The amount of alkaline phosphatase in each well was determined by standard methods. A similar ELISA procedure for use in the peptides on plasmids system is described in detail below.

By comparing test wells with control wells (no receptor), one can determine whether the fusion proteins bind to the receptor specifically. The phage pools found to bind to IL-5R were screened in a colony lift probing format using bivalent IL-5R probes. This probe was constructed by pre-incubating radiolabeled Ab 179 with the receptor. The complex was subsequently purified over an immobilized Ab 179 affinity column to separate the complex from free receptor.

Peptides found to bind specifically to the receptor were then tested for their ability to block the binding of IL-5 to its receptor using an ELISA format. Peptides found to both block and bind were then synthesized as the free peptide (no phage) and tested in an IL-5 blocking assay using radiolabelled IL-5. The blocking assay was carried out in similar fashion to the ELISA, except that IL-5 was added to the wells before the fusion protein (the control wells were of two types: (1) no receptor; and (2) no IL-5). Fusion proteins for which the binding to the receptor was blocked by IL-5 contain peptides in the random peptide portion that are preferred compounds of the invention.

The immobilized α chain, β chain, and heterodimer, as well as the extracellular domains of the single chains of the IL-5 receptors were produced in recombinant host cells. The DNA encoding IL-5R was obtained by PCR of cDNA from TF-1 cells using primers obtained from the published receptor sequences. See Murata (1992) *J. Exp. Med.* 175:341–351 and Hayashida (1990) *Proc. Natl. Acad. Sci. USA* 87:9655–9659, each of which is incorporated herein by reference. One useful form of IL-5R is constructed by expressing the protein as a soluble protein inbaculovirus transformed host cells using standard methods; another useful form is constructed with a signal peptide for protein secretion and for glycophospholipid membrane anchor attachment. This form of anchor attachment is called "PIG-tailing". See Caras and Wendell (1989) *Science* 243:1196–1198 and Lin et al. (1990) *Science* 249:677–679.

Using the PIG-tailing system, one can cleave the receptor from the surface of the cells expressing the receptor (e.g., transformed CHO cells selected for high level expression of receptor with a cell sorter) with phospholipase C. The cleaved receptor still comprises a carboxy terminal sequence of amino acids, called the "HPAP tail", from the signal protein for membrane attachment and can be immobilized without further purification. The recombinant receptor protein can be immobilized by coating the wells of microtiter plates with an anti-HPAP tail antibody (Ab 179), blocking non-specific binding with bovine serum albumin (BSA) in PBS, and then binding cleaved recombinant receptor to the antibody. Using this procedure, one should perform the immobilization reaction in varying concentrations of receptor to determine the optimum amount for a given preparation, because different preparations of recombinant protein often contain different amounts of the desired protein. In addition, one should ensure that the immobilizing antibody is completely blocked (with IL-5R or some other blocking compound) during the affinity enrichment process. Otherwise, unblocked antibody can bind undesired phage during the affinity enrichment procedure. One can use peptides that bind to the immobilizing antibody to block unbound sites that remain after receptor immobilization to avoid this problem or one can simply immobilize the receptor directly to the wells of microtiter plates, without the aid of an immobilizing antibody. See U.S. patent application Ser. No. 07/947,339, filed Sep. 18, 1992, incorporated herein by reference.

When using random peptide generation systems that allow for multivalent ligand-receptor interaction, one must recognize that the density of the immobilized receptor is an important factor in determining the affinity of the ligands that can bind to the immobilized receptor. At higher receptor densities (e.g., each anti-receptor antibody-coated well treated with 0.25 to 0.5 μg of receptor), multivalent binding is more likely to occur than at lower receptor densities (e.g., each anti-receptor antibody-coated well treated with 0.5 to 1 ng of the receptor). If multivalent binding is occurring, then one will be more likely to isolate ligands with relatively lower affinity, unless one uses high densities of immobilized receptor to identify lead compounds and uses lower receptor densities to isolate derivative compounds with higher affinity for the receptor than the lead compounds.

To discriminate among higher affinity peptides, a monovalent receptor probe frequently is used. This probe can be produced using protein kinase A to phosphorylate a kemptide sequence fused to the C-terminus of the soluble receptor. The "engineered" form of the IL-5 receptor α and β chains are then expressed in host cells, typically CHO cells. Following PI-PLC harvest of the receptors, the receptor is labeled to high specific activity with $^{33}P$ for use as a monovalent probe to identify high affinity ligands using colony lifts.

Preferred screening methods to facilitate identification of peptides which bind IL-5R involve first identifying lead peptides which bind the receptor and then making other peptides which resemble the lead peptides. Specifically, using a pIII or pVIII-based peptides on phage system, a random library can be screened to discover a phage that presents a peptide that binds to IL-5R. The phage DNAs are sequenced to determine the sequences of the peptides displayed on the surface of the phages. Examples of primary libraries which were produced and panned against immobilized IL-5R α ECD include: GGC(X)$_{10}$C(G$_4$S)$_3$ (SEQ ID NO:10); GGC(X)$_{12}$C(G$_4$S)$_3$ (SEQ ID NO:11); XXXC(X)$_5$CXXX(G$_4$S)$_3$ (SEQ ID NO:12); XXXC(X)$_6$CXXX(G$_4$S)$_3$ (SEQ ID NO:13); XXXC(X)$_7$CXXX(G$_4$S)$_3$ (SEQ ID NO:14); XXXC(X)$_8$CXXX(G$_4$S)$_3$ (SEQ ID NO:15); XXXC(X)$_9$CXXX(G$_4$S)$_3$ (SEQ ID NO:16); and XXXC(X)$_{10}$CXXX(G$_4$S)$_3$ (SEQ ID NO:17), wherein X represents random residue encoded by NNK; and (G$_4$S)$_3$ (SEQ ID NO:18) is a peptide linker.

α-Chain specific clones and clones capable of specific binding to the β-chain of IL-5R were identified. The sequences of these peptides serve as the basis for the construction of other peptide libraries designed to contain a high frequency of derivatives of the initially identified peptides. These libraries can be synthesized so as to favor the production of peptides that differ from the binding peptide in only a few residues. This approach involves the synthesis of an oligonucleotide with the binding peptide coding sequence, except that rather than using pure preparations of each of the four nucleoside triphosphates in the synthesis, one uses mixtures of the four nucleoside triphosphates (i.e., 55% of the "correct" nucleotide, and 15% each of the other three nucleotides is one preferred mixture for this purpose and 70% of the "correct" nucleotide and 10% of each of the other three nucleotides is another preferred mixture for this purpose) so as to generate derivatives of the binding peptide coding sequence.

A variety of mutagenesis strategies were used to derivatize the lead peptides by making "mutagenesis on a theme" libraries, which included mutagenesis of the original coding sequences at 70:10:10:10 frequencies with 3 NNK codons on each terminus (panned for 3 rounds against the immobilized extracellular domain (ECD) of the IL-5 receptor α chain (IL-5R α) in the presence of known binding peptide; alternatively, known binding peptide was included during the wash step); fixed-sliding libraries, such as X X X X X X X W R V P C G G (SEQ ID NO:19); and G G C W S G E X X X X X X X X (SEQ ID NO:20 ) (panned for 3 rounds against the immobilized extracellular domain (ECD) of the IL-5 receptor α chain (IL-5R α) in the presence of known binding peptide; alternatively, known binding peptide was included during the wash step; screened by colony lift using a bivalent receptor probe of the IL-5R α chain complexed with mAb 179); and extended/mutagenized libraries.

In addition, the various phage libraries can be rescreened against IL-5R α in the presence of known binding peptide or non-IL-5 competitive peptide during the final wash or at room temperature or 4° C. to identify peptides of higher affinity. Pools of phage are then probed by colony lift using $^{32}$p labeled IL-5R α (as discussed above).

A plasmid library expressing peptides of the form: $X_3CX_{(5-10)}CX_3$ (where X is a random residue encoded by an NNK codon and C is a fixed cysteine residue) was screened against the ECD of the IL-5 receptor α chain. Clones were examined for receptor specific binding by LacI ELISA. The binding of all of the clones was blocked by preincubation of the receptor with 10 nM IL-5. The enriched pools of clones were transferred to a maltose binding protein (MBP) fusion expression system and the MBP-peptide fusions were tested for receptor specific binding using an MBP ELISA that has been shown to be more selective for higher affinity peptides than the Lad ELISA. This MBP ELISA identified one of the previously identified clones as well as a new clone, which was also competed by IL-5 for receptor binding. A LacI ELISA was then performed in which the receptor was preincubated with 250 μM of a known IL-5 binding peptide prior to the addition of the LacI-peptide fusions. Binding of all but one of the clones tested was blocked by the peptide.

In addition, libraries with fixed amino acids, such as V E V C T R S V A T H S W V C G I D (SEQ ID NO:21); X G Y V C V E W A R C Q T C X (SEQ ID NO:22); X L R G C R E R Y M L C V S D X (SEQ ID NO:23); and R X X C 12 X X X X X X X X X X X X X (SEQ ID NO:24) (lowercase=70:10:10:10 nucleotide misincorporation; uppercase=fixed residue; X=random residue encoded by NNK; 1=I, L, F, V, or M encoded by NTK codon; 2=G, R, S, or C encoded by NGT codon), were produced in using the affinity selective headpiece dimer display system and tested under standard and low receptor density conditions. Three of the libraries were 70:10:10:10 codon mutagenesis libraries and the fourth library was based on a common sequence motif seen in a number of plasmid derived clones. All of the libraries contained >$10^9$ members. These libraries were panned against the IL-5R α ECD for four rounds, optionally with the addition of IL-5 during the washes. Pools of clones showing binding to the receptor were transferred from the headpiece dimer expression plasmid into a maltose binding protein (MBP) fusion expression system in order to probe for high affinity clones using $^{32}$P labeled monovalent receptor probe in a colony lift assay.

The "peptides on plasmids" techniques was also used for peptide screening and mutagenesis studies and is described in greater detail in U.S. Pat. No. 5,338,665, which is incorporated herein by reference for all purposes. According to this approach, random peptides are fused at the C-terminus of LacI through expression from a plasmid vector carrying the fusion gene. Linkage of the LacI-peptide fusion to its encoding DNA occurs via the lacO sequences on the plasmid, forming a stable peptide-Lad-plasmid complex that can be screened by affinity purification (panning) on an immobilized receptor. The plasmids thus isolated can then be reintroduced into *E. coli* by electroporation to amplify the selected population for additional rounds of screening, or for the examination of individual clones.

In addition, random peptide screening and mutagenesis studies were performed using a modified C-terminal Lac-I display system in which display valency was reduced ("headpiece dimer" display system). The libraries were screened and the resulting DNA inserts were cloned as a pool into a maltose binding protein (MBP) vector allowing their expression as a C-terminal fusion protein. Crude cell lysates from randomly picked individual MBP fusion clones were then assayed for TPO-R binding in an ELISA format, as discussed above.

Screening of the various phage and plasmid libraries described above yielded the IL-5 receptor binding peptides shown in Table 1 below, as well as others not listed herein.

TABLE 1

| Peptide |
|---|
| D G Y V C V E W A R C P T C K (SEQ ID NO:7) |
| D G Y V C V E W A R C P K C X (SEQ ID NO:25) |
| D G Y V C G E W V X C P S C T (SEQ ID NO:26) |
| D G F V C V E W A R C P N C R (SEQ ID NO:9) |
| D G Y V C V E W A R C P M C T (SEQ ID NO:8) |
| D G Y V C V E W V R C P T C R (SEQ ID NO:27) |
| D G W V C V E W V R C Q T C Y (SEQ ID NO:28) |
| E G Y V C V E W A R C P S C K (SEQ ID NO:29) |
| E G Y V C V E W A R C P S C V (SEQ ID NO:30) |
| E G W V C V E W A R C P T C L (SEQ ID NO:31) |
| G G W V C V D W A R C P T C L (SEQ ID NO:32) |
| G G Y V C V E W A R C P S C Q (SEQ ID NO:33) |
| I G W V C V E W A R C P A C K (SEQ ID |

TABLE 1-continued

| Peptide |
| --- |
| NO:34) |
| M G W V C V E W A R C P T C L (SEQ ID NO:35) |
| N G Y V C V E W A R C P M C K (SEQ ID NO:36) |
| N G W V C V D W A R C P S C R (SEQ ID NO:37) |
| N G Y V C I E W A R C P S C R (SEQ ID NO:38) |
| N G Y V C V E W A R C P S C I (SEQ ID NO: 39) |
| N G Y V C Y E W A R C P M C K (SEQ ID NO:40) |
| P G Y V C V D W A R C P E C R (SEQ ID NO:41) |
| Q G Y V C V E W A R C P M C T (SEQ ID NO:42) |
| Q G Y V C V E W A R C P S C M (SEQ ID NO:43) |
| S G W V C V E W A R C P S C I (SEQ ID NO:44) |
| V G Y V C V E W A R C P M C R (SEQ ID NO:45) |
| P G Y V C V D W A R C P M C K (SEQ ID NO:46) |
| P G Y V C V D W A R C P M C Q (SEQ ID NO:47) |
| P G Y V C V E W A R C P A C K (SEQ ID NO:48) |
| P V Y V C V D W A R C P M C Q (SEQ ID NO:49) |
| Q G W V C V E W A R C P T C E (SEQ ID NO:50) |
| V G Y V C V E W A R C P T C I (SEQ ID NO:51) |
| Y G Y V C V D W A R C P E C R (SEQ ID NC:52) |
| G Y V C V E W A R C Q T C (SEQ ID NC:53) |

$IC_{50}$ values for some additional representative peptides are given the table below. A variety of methods can be used to evaluate $IC_{50}$ values. For example, an [125-I] IL-5 binding assay was used to determine whether the peptides inhibit the binding of IL-5 to the extracellular domain of the IL-5 receptor α-chain, as described in Example 3 below. Alternatively, for some peptides, a microphysiometer assay was used to determine whether the peptide blocked the response of TF-1 cells to IL-5 (5 ng/ml), as described in Example 2 below.

The $IC_{50}$ value can be determined using the free peptide, which optionally can be C-terminally amidated, or can be prepared as an ester or other carboxy amide. For peptides identified from peptides on plasmids libraries, the $IC_{50}$ values were typically evaluated on both the parent MBP-fusion and the corresponding synthetic peptide. To recreate the exact sequence of the peptide displayed by the phage, the N-terminal and C-terminal amino acids of the synthetic peptides are often preceded by one or two glycine residues. These glycines are not believed to be necessary for binding or activity.

$IC_{50}$ values are indicated symbolically by the symbols "−", "+", and "++". For examples, those peptides which showed $IC_{50}$ values in excess of 100 µM are indicated with a "−". Those peptides which gave $IC_{50}$ values of less than or equal to 100 µM are given a "+", while those which gave $IC_{50}$ values of 500 nm or less are indicated with a "++". Those peptides which gave $IC_{50}$ values at or near the cutoff point for a particular symbol are indicated with a hybrid designator, e.g., "±". Those peptides for which $IC_{50}$ values were not determined are listed as "N.D.".

TABLE 2

| Peptide | Affinity |
| --- | --- |
| D G Y V C V E W A R C P T C K (SEQ ID NO: 7) | ++ |
| D G Y V C V E W A R C P M C T (SEQ ID NO: 8) | ++ |
| D G F V C V E W A R C P N C R (SEQ ID NO: 9) | ++ |

The tables above illustrate that a preferred core peptide comprises a sequence of amino acids:

$$C\ X_1\ X_2\ W\ X_3\ R\ C\ X_4\ X_5\ C$$

where $X_1$ is G, I, V, or Y; $X_2$ is D or E; X3 is A or V; X4 is Q or P; and $X_5$ is A, E, K, M, N, S, or T (SEQ ID NO:1). Preferably, the core peptide comprises a sequence of amino acids:

$$C\ X_1\ X_2\ W\ X_3\ R\ C\ X_4\ X_5\ C$$

where $X_1$ is V; $X_2$ is E; $X_3$ is A; $X_4$ is P (SEQ ID NO:2). More preferably, the core peptide comprises either a sequence of amino acids:

$$X_6\ X_7\ X_8\ V\ C\ X_1\ X_2\ W\ X_3\ R\ C\ X_4\ X_5\ C$$

where $X_6$ is D, E, G, I, M, N, P, Q, S, V, or Y; $X_7$ is G, V, or Y; and $X_8$ is F, W, or Y (SEQ ID NO:3); or a sequence of amino acids:

$$C\ X_1\ X_2\ W\ X_3\ R\ C\ X_4\ X_5\ C\ X_9$$

where $X_9$ is E, I, K, L, M, Q, R, T, V, or Y (SEQ ID NO:4). Preferably, the core peptide comprises a sequence of amino acids:

$$X_6\ X_7\ X_8\ V\ C\ X_1\ X_2\ W\ X_3\ R\ C\ X_4\ X_5\ C\ X_9\ (SEQ\ ID\ NO:65)$$

More preferably, $X_6$ is D, E, G, N, P, or Q; $X_7$ is G; and $X_{10}$ is K, L, Q, R, or T (SEQ ID NO:5). Most preferably, $X_6$ is D, N, or P; $X_8$ is F or Y; and $X_{10}$ is K, R, or T (SEQ ID NO:6).

Preferred peptides include those listed in the tables above. Particularly preferred peptides include: D G Y V C V E W A R C P T C K (SEQ ID NO:7); D G Y V C V E W A R C P M C T (SEQ ID NO:8); and D G F V C V E W A R C P N C R (SEQ ID NO:9).

Peptides and peptidomimetics having an $IC_{50}$ of greater than about 100 mM lack sufficient binding to permit use in either the diagnostic or therapeutic aspects of this invention. Preferably, for diagnostic purposes, the peptides and peptidomimetics have an $IC_{50}$ of about 2.5 mM or less and, for pharmaceutical purposes, the peptides and peptidomimetics have an $IC_{50}$ of about 2 mM or less.

The binding peptide sequence also provides a means to determine the minimum size of an IL-5R binding compound of the invention. Using the "encoded synthetic library" (ESL) system described in U.S. patent application Ser. No. 946,239, filed Sep. 16, 1992, which is a continuation-in-part application of Ser. No. 762,522, filed Sep. 18, 1991, or the "very large scale immobilized polymer synthesis" system described in U.S. patent application Ser. Nos. 492,462, filed Mar. 7, 1990; 624,120, filed Dec. 6, 1990; and 805,727, filed Dec. 6, 1991; one can not only determine the minimum size of a peptide with such activity, but one can also make all of the peptides that form the group of peptides that differ from the preferred motif (or the minimum size of that motif) in one, two, or more residues. This collection of peptides can then be screened for ability to bind to IL-5 receptor. These immobilized polymers synthesis systems or other peptide synthesis methods can also be used to synthesize truncation analogs, deletion analogs, substitution analogs, and combinations thereof all of the peptide compounds of the invention.

The peptides of the invention can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield (1963) *J. Am. Chem. Soc.* 85:2149, incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky et al., (1966) *Chem. Ind.* (London) 38:1597. The benzhydrylamine (BHA) resin has been described by Pietta and Marshall (1970) *Chem. Commn.* 650, and is commercially available from Beckman Instruments, Inc., Palo Alto, Calif., in the hydrochloride form.

Thus, the compounds of the invention can be prepared by coupling an alpha-amino protected amino acid to the chloromethylated resin with the aid of, for example, cesium bicarbonate catalyst, according to the method described by Gisin (1973) *Helv. Chim. Acta* 56:1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e.g. formyl, trifluoroacetyl, acetyl), aromatic urethane type protecting groups (e.g. benzyloxycarboyl (Cbz) and substituted Cbz), aliphatic urethane protecting groups (e.g. t-butyloxycarbonyl (Boc), isopropyloxycarbonyl, cyclohexyloxycarbonyl) and alkyl type protecting groups (e.g. benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

In preparing the compounds of the invention, the resins used to prepare the peptide acids are employed, and the side chain protected peptide is cleaved with base and the appropriate alcohol, i.e., methanol. Side chain protecting groups are then removed in the usual fashion by treatment with hydrogen fluoride to obtain the desired ester. These solid phase peptide synthesis procedures are well known in the art and further described in Stewart, *Solid Phase Peptide Syntheses* (Freeman and Co., San Francisco, 1969).

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3, 4-dihydroxyphenylalanyl, $\partial$ amino acids such as L-$\partial$-hydroxylysyl and D-$\partial$-methylalanyl, L-$\alpha$-methylalanyl, $\beta$ amino acids, and isoquinolyl. D amino acids and non-naturally occurring synthetic amino acids can also be incorporated into the peptides of the present invention.

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered hetereocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic.

The peptides typically are synthesized as the free acid but, as noted above, could be readily prepared as the amide or ester. One can also modify the amino and/or carboxy terminus of the peptide compounds of the invention to produce other compounds of the invention. Amino terminus modifications include methylating (i.e., —$NHCH_3$ or —$NH(CH_3)_2$), acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. Specifically, the N-terminal amino group can then be reacted as follows:

(a) to form an amide group of the formula RC(O)NH— where R is as defined above by reaction with an acid halide [e.g., RC(O)Cl] or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (e.g., about 5 equivalents) can be employed and the amino group is converted to the succinimide by methods well known in the art including the use of an excess (e.g., ten equivalents) of a tertiary amine such as diisopropylethylamine in a suitable inert solvent (e.g., dichloromethane). See, for example, Wollenberg, et al., U.S. Pat. No. 4,612,132 which is incorporated herein by reference in its entirety. It is understood that the succinic group can be substituted with, for example, $C_2$–$C_6$ alkyl or —SR substituents which are prepared in a conventional manner to provide for substituted succinimide at the N-terminus of the peptide. Such alkyl substituents are prepared by reaction of a lower olefin ($C_2$–$C_6$) with maleic anhydride in the manner described by Wollenberg, et al., supra. and —SR substituents are prepared by reaction of RSH with maleic anhydride where R is as defined above;

(c) to form a benzyloxycarbonyl—NH— or a substituted benzyloxycarbonyl—NH— group by reaction with approximately an equivalent amount or an excess of CBZ-Cl (i.e., benzyloxycarbonyl chloride) or a substituted CBZ-Cl in a suitable inert diluent (e.g., dichloromethane) preferably containing a tertiary amine to scavenge the acid generated during the reaction;

(d) to form a sulfonamide group by reaction with an equivalent amount or an excess (e.g., 5 equivalents) of R—S(O)$_2$Cl in a suitable inert diluent (dichloromethane) to convert the terminal amine into a sulfonamide where R is as defined above. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes);

(e) to form a carbamate group by reaction with an equivalent amount or an excess (e.g., 5 equivalents) of R—OC(O)Cl or R—OC(O)OC$_6$H$_4$—p—NO$_2$ in a suitable inert diluent (e.g., dichloromethane) to convert terminal amine into a carbamate where R is as defined above. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes); and (f) to form a urea group by reaction with an equivalent amount or an excess (e.g., 5 equivalents) of R—N═C═O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

In preparing peptide mimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester.

In preparing peptide mimetics wherein the C-terminal carboxyl group is replaced by the amide —C(O)NR$^3$R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the terminii of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can also readily modify peptides by phosphorylation, and other methods for making peptide derivatives of the compounds of the present invention are described in Hruby et al., (1990) *Biochem J.* 268(2):249–262, incorporated herein by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan and Gainor (1989) *Ann. Rep. Med. Chem.* 24:243–252, incorporated herein by reference. These techniques include replacing the peptide backbone with a backbone composed of phosphonates, amidates, carbamates, sulfonamides, secondary amines, and N-methylamino acids.

Peptide mimetics wherein one or more of the peptidyl linkages [—C(O)NH—] have been replaced by such linkages as a —$CH_2$—carbamate linkage, a phosphonate linkage, a —$CH_2$—sulfonamide linkage, a urea linkage, a secondary amine (—$CH_2NH$—) linkage, and an alkylated peptidyl linkage [—C(O)$NR^6$— where $R^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O)NR— linkage in the peptide with a —$CH_2$—carbamate linkage (—$CH_2OC(O)NR$—), then the carboxyl (—COOH) group of a suitably protected amino acid is first reduced to the —$CH_2OH$ group which is then converted by conventional methods to a —OC(O)Cl functionality or a para-nitrocarbonate —OC(O)O—$C_6H_4$—p—$NO_2$ functionality. Reaction of either of such functional groups with the free amine or an alkylated amine on the N-terminus of the partially fabricated peptide found on the solid support leads to the formation of a —$CH_2OC(O)NR$— linkage. For a more detailed description of the formation of such —$CH_2$—carbamate linkages, see Cho et al, *Science,* 261:1303–1305 (1993).

Similarly, replacement of an amido linkage in the peptide with a phosphonate linkage can be achieved in the manner set forth in U.S. patent application Ser. Nos. 07/943,805, 08/081,577, and 08/119,700, the disclosures of which are incorporated herein by reference in their entirety.

Replacement of an amido linkage in the peptide with a —$CH_2$—sulfonamide linkage can be achieved by reducing the carboxyl (—COOH) group of a suitably protected amino acid to the —$CH_2OH$ group and the hydroxyl group is then converted to a suitable leaving group such as a tosyl group by conventional methods. Reaction of the tosylated derivative with, for example, thioacetic acid followed by hydrolysis and oxidative chlorination will provide for the —$CH_2$—$S(O)_2Cl$ functional group which replaces the carboxyl group of the otherwise suitably protected amino acid. Use of this suitably protected amino acid analogue in peptide synthesis provides for inclusion of an —$CH_2S(O)_2NR$— linkage which replaces the amido linkage in the peptide thereby providing a peptide mimetic. For a more complete description on the conversion of the carboxyl group of the amino acid to a —$CH_2S(O)_2Cl$ group, see, for example, *Chemistry & Biochemistry of Amino Acids, Peptides and Proteins,* Boris Weinstein (ed.), Vol. 7, pp. 267–357, Marcel Dekker, Inc., New York (1983) which is incorporated herein by reference.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a —$CH_2NH$— linkage replaces the amido linkage in the peptide can be prepared by employing, for example, a suitably protected dipeptide analogue wherein the carbonyl bond of the amido linkage has been reduced to a $CH_2$ group by conventional methods. For example, in the case of diglycine, reduction of the amide to the amine will yield after deprotection $H_2NCH_2CH_2NHCH_2COOH$ which is then used in N-protected form in the next coupling reaction. The preparation of such analogues by reduction of the carbonyl group of the amido linkage in the dipeptide is well known in the art.

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10 fold excess. The reaction results in incorporation into the peptide mimetic of an amino acid analogue having a non-peptidyl linkage. Such substitution can be repeated as desired such that from zero to all of the amido bonds in the peptide have been replaced by non-amido bonds.

One can also cyclize the peptides of the invention, or incorporate a desamino or descarboxy residue at the terminii of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

The compounds of the present invention may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine. These intramolecular or intermolecular disulfide derivatives can be represented schematically as shown below:

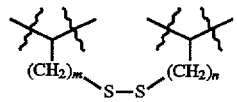

wherein m and n are independently 1 or 2.

Other embodiments of this invention provide for analogs of these disulfide derivatives in which one of the sulfurs has been replaced by a $CH_2$ group or other isostere for sulfur. These analogs can be made via an intramolecular or intermolecular displacement, using methods known in the art as shown below:

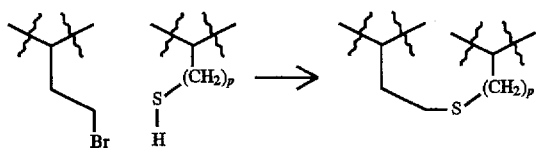

wherein p is 1 or 2. One of skill in the art will readily appreciate that this displacement can also occur using other homologs of the α-amino-γ-butyric acid derivative shown above and homocysteine.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The compounds of the present invention can be cyclized or dimerized via displacement of the leaving group by the sulfur of the cysteine or homocysteine residue. See, e.g., Barker et al. (1992) *J. Med. Chem.* 35:2040–2048 and Or et al. (1991) *J. Org. Chem.* 56:3146–3149, each of which is incorporated herein by reference.

Using the "very large scale immobilized polymer synthesis" system described in U.S. patent application Ser. Nos. 492,462, filed Mar. 7, 1990; 624,120, filed Dec. 6, 1990; and 805,727, filed Dec. 6, 1991; one can not only determine the minimum size of a peptide with such activity, one can also make all of the peptides that form the group of peptides that differ from the preferred motif (or the minimum size of that motif) in one, two, or more residues. This collection of peptides can then be screened for ability to bind to IL-5R. This immobilized polymer synthesis system or other peptide synthesis methods can also be used to synthesize every truncation analog and every deletion analog and every combination of truncation and deletion analog of all of the peptide compounds of the invention.

IV. In Vivo and In Vitro Testing

The activity of the compounds of the present invention can be evaluated in vivo in one of the numerous animal models of asthma. See Larson, "Experimental Models of Reversible Airway Obstruction", in *The Lung: Scientific Foundations,* Crystal, West et al., eds., Raven Press, New York, 1991; Warner et al. (1990) *Am. Rev. Respir. Dis.* 141:253–257. An ideal animal model would duplicate the chief clinical and physiological features of human asthma, including: airway hyperresponsiveness to chemical mediators and physical stimuli; reversal of airway obstruction by drugs useful in human asthma (β-adrenergics, methylxanthines, corticosteroids, and the like); airway inflammation with infiltration of activated leukocytes; and chronic inflammatory degenerative changes, such as basement membrane thickening, smooth muscle hypertrophy, and epithelial damage. Species used historically as animal models include mice, rats, guinea pigs, rabbits, dogs, and sheep. All have some limitations, and the proper choice of animal model depends upon the question which is to be addressed.

The initial asthmatic response can be evaluated in guinea pigs, and dogs, and particularly, with a basenji-greyhound cross strain which develops nonspecific airway hyperresponsiveness to numerous nonallergenic substances, such as methacholine and citric acid. Certain selected sheep exhibit a dual response after antigen challenge with Ascaris proteins. In dual responding animals, the initial asthmatic response (IAR) is followed by a late asthmatic response (LAR) at 6–8 hours post-exposure. Hypersensitivity to the cholinergic agonist carbachol increases at 24 hours after antigen challenge in those animals which exhibit LAR.

The allergic sheep model can be used to evaluate the potential antiasthmatic effects of the compounds of the present invention. Administration of compositions comprising aerosolized solutions of the compounds of the instant invention to allergic sheep prior to or following exposure to specific allergens will demonstrate that such compositions substantially lessen or abolish the late asthmatic response and consequent hyperresponsiveness.

The compounds of this invention are also useful for the treatment of other immunomediated inflammatory disorders in which tryptase activity contributes to the pathological condition. Such diseases include inflammatory diseases associated with mast cells, such as rheumatoid arthritis, rheumatoid spondylitis, osteoarthritis, gouty arthritis and other arthritic conditions, inflammatory bowel disease, peptic ulcer and various skin conditions.

The efficacy of the compounds of the instant invention for the treatment of the vast majority of immunomediated inflammatory disorders can be evaluated by either in vitro or in vivo procedures. Thus, the anti-inflammatory efficacy of the compounds of the instant invention can be demonstrated by assays well known in the art, for example, the Reversed Passive Arthus Reaction (RPAR)-PAW technique (see, e.g., Ganguly et al. (1992) U.S. Pat. No. 5,126,352). Assays for determining the therapeutic value of compounds in the treatment of various skin conditions, such as hyperproliferative skin disease, are well known in the art, for example, the Arachidonic Acid Mouse Ear Test (id). The compounds of the instant invention can be evaluated for their antiulcer activity according to the procedures described in Chiu et al. (1984) *Archives Internationales de Pharmacodynamie et de Therapie* 270.:128–140.

IV. In Vitro Uses

The compounds of the invention are useful in vitro as unique tools for understanding the biological role of IL-5, including the evaluation of the many factors thought to influence, and be influenced by, the production of IL-5 and the receptor binding process. The present compounds are also useful in the development of other compounds that bind to the IL-5R, because the present compounds provide important information on the relationship between structure and activity that should facilitate such development.

The compounds are also useful as competitive inhibitors or tracers in assays to screen for new IL-5 receptor blockers. In such assay embodiments, the compounds of the invention can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Thus, the compositions and methods of the present invention also can be used in vitro for testing a patient's susceptibility to varying treatment regimens for disorders associated with the overproduction of IL-5 or an improper response to IL-5 using an in vitro diagnostic method whereby a specimen is taken from the patient and is treated with a IL-5R binding, IL-5 blocking compound of the present invention to determine the effectiveness and amount of the compound necessary to produce the desired effect. The blocking compound and dosage can be varied. After the blocking compounds are screened, then the appropriate treatment and dosage can be selected by the physician and administered to the patient based upon the results. Therefore, this invention also contemplates use of a blocking compound of this invention in a variety of diagnostic kits and assay methods.

V. In Vivo Uses

The compounds of the invention can also be administered to warm blooded animals, including humans, to block the binding of IL-5 to the IL-5R in vivo. Thus, the present invention encompasses methods for therapeutic treatment of IL-5 related disorders that comprise administering a compound of the invention in amounts sufficient to block or inhibit the binding of IL-5 to the IL-5R in vivo. For example, the peptides and compounds of the invention can be administered to treat symptoms related to the overproduction of IL-5 or an improper response to IL-5. The compositions and methods described herein will find use for the treatment and/or prevention of a variety of IL-5 related disorders.

According to one embodiment, the compositions of the present invention are useful for preventing or ameliorating asthma. In using the compositions of the present invention in a treatment of asthma, the compounds typically will be administered prophylactically prior to exposure to allergen or other precipitating factor, or after such exposure. The compounds of the instant invention are particularly useful in ameliorating the late-phase tissue destruction seen in both seasonal and perennial rhinitis. Another aspect of the present invention is directed to the prevention and treatment of other immunomediated inflammatory disorders associated with mast cells such as urticaria and angioedema, and eczematous dermatitis (atopic dermatitis), and anaphylaxis, as well as hyperproliferative skin disease, peptic ulcers, and the like.

Accordingly, the present invention also provides pharmaceutical compositions comprising, as an active ingredient, at least one of the peptides or peptide mimetics of the invention in association with a pharmaceutical carrier or diluent. The compounds of this invention can be administered by oral, pulmonary, parental (intramuscular, intraperitoneal, intravenous (IV) or subcutaneous injection), inhalation (via a fine powder formulation). transdermal, nasal, vaginal, rectal, or sublingual routes of administration and can be formulated in dosage forms appropriate for each route of administration.

Typically, when the compounds of the instant invention are to be used in the treatment of asthma, they will be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

For solutions used in making aerosols of the present invention, the preferred range of concentration of the compounds of the instant invention is 0.1–100 milligrams (mg)/milliliter (mL), more preferably 0.1–30 mg/mL, and most preferably, 1–10 mg/mL. Usually the solutions are buffered with a physiologically compatible buffer such as phosphate or bicarbonate. The usual pH range is 5 to 9, preferably 6.5 to 7.8, and more preferably 7.0 to 7.6. Typically, sodium chloride is added to adjust the osmolarity to the physiological range, preferably within 10% of isotonic. Formulation of such solutions for creating aerosol inhalants is discussed in Remington's Pharmaceutical Sciences, see also, Ganderton and Jones, Drug Delivery to the Respiratory Tract, Ellis Horwood (1987); Gonda (1990) Critical Reviews in Therapeutic Drug Carrier Systems 6:273–313; and Raeburn et al. (1992) J. Pharmacol. Toxicol. Methods 27:143–159.

Solutions of the compounds of the instant invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the instant invention connected to or contained within any of the conventional means for creating aerosols in asthma medication, such as metered dose inhalers, jet nebulizers, or ultrasonic nebulizers. Optionally such device may include a mouthpiece fitted around the orifice.

In an embodiment for the treatment of allergic rhinitis, a device may comprise a solution of a compound of the instant invention in a nasal sprayer.

A dry powder comprising a compound of the instant invention, optionally with an excipient, is another embodiment of the present invention. This may be administered by a drug powder inhaler containing the above described powder.

The compounds of the inventions can also be used in the treatment of immunomediated inflammatory skin conditions, such as urticaria and angioedema, eczematous dermatitis, and hyperproliferative skin disease, e.g., psoriasis, in mammals. As a result of the topical administration of a compound of the present invention, a remission of the symptoms can be expected. Thus, one affected by an immunomediated inflammatory skin condition can expect a decrease in scaling, erythema, size of the plaques, pruritus, and other symptoms associated with the skin condition. The dosage of medicament and the length of time required for successfully treating each individual patient may vary, but those skilled in the art will be able to recognize these variations and adjust the course of therapy accordingly.

Also included within the invention are preparations for topical application to the skin comprising a compound of the present invention, typically in concentrations in the range of from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

It should, of course, be understood that the compositions and methods of this invention can be used in combination with other agents exhibiting the ability to modulate IL-5 synthesis, release, and/or binding and with other agents for the treatment of immunomediated inflammatory disorders, and particularly asthma. β-Adrenergic agonists are especially useful in these combinations, because they provide symptomatic relief of the initial asthmatic response, whereas the compounds of the present invention provide relief for the late asthmatic response. Preferred β-adrenergic agonists in these solutions include any of the usual β-agonists employed for the relief of asthma, such as albuterol, terbutaline, formoterol, fanoterol, or prenaline.

Other agents useful in combination with the compounds of the instant invention include anticholinergics, such as ipratropium bromide, and antiinflammatory corticosteroids (adrenocortical steroids) such as beclomethasone, triamcinolone, flurisolide, or dexamethasone.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

The quantities of the IL-5 blocking compound necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), (1990) *Goodman and Gilman's: The Pharmacological Basis of Therapeutics*, 8th ed., Pergamon Press; and *Remington's Pharmaceutical Sciences*, (1985) 7th ed., Mack Publishing Co., Easton, Pa.; each of which is hereby incorporated by reference.

The peptides and peptide mimetics of this invention are effective in treating IL-5 mediated conditions when administered at a dosage range of from about 0.001 mg to about 10 mg/kg of body weight per day. The specific dose employed is regulated by the particular condition being treated, the route of administration as well as by the judgement of the attending clinician depending upon factors such as the severity of the condition, the age and general condition of the patient, and the like.

Although only preferred embodiments of the invention are specifically described above, it will be appreciated that modifications and variations of the invention are possible without departing from the spirit and intended scope of the invention.

EXAMPLE 1

Solid Phase Peptide Synthesis

Various peptides of the invention were synthesized using the Merrifield solid phase synthesis techniques (see Steward and Young, *Solid Phase Peptide Synthesis*, 2d. edition (Pierce Chemical, Rockford, Ill. (1984) and Merrifield (1963) *J. Am. Chem. Soc.* 85:2149) on a Milligen/Biosearch 9600 automated instrument or an Applied Biosystems Inc. Model 431A peptide synthesizer. The peptides were assembled using standard protocols of the Applied Biosystems Inc. System Software version 1.01. Each coupling was performed for one-two hours with BOP (benzotriazolyl N-oxtrisdimethylaminophosphonium hexafluorophosphate) and HOBt (1-hydroxybenzotriazole).

The resin used was HMP resin or PAL (Milligen/Biosearch), which is a cross-linked polystyrene resin with 5-(4'-Fmoc-aminomethyl-3,5'-dimethyoxyphenoxy)valeric acid as a linker. Use of PAL resin results in a carboxyl terminal amide functionality upon cleavage of the peptide from the resin. Upon cleavage, the HMP resin produces a carboxylic acid moiety at the C-terminus of the final product. Most reagents, resins, and protected amino acids (free or on the resin) were purchased from Millipore or Applied Biosystems Inc.

The Fmoc group was used for amino protection during the coupling procedure. Primary amine protection on amino acids was achieved with Fmoc and side chain protection groups were t-butyl for serine, tyrosine, asparagine, glutamic acid, and threonine; trityl for glutamine; Pmc (2,2,5,7,8-pentamethylchroma sulfonate) for arginine; N-t-butyloxycarbonyl for tryptophan; N-trityl for histidine and glutamine; and S-trityl for cysteine.

Removal of the peptides from the resin and simultaneous deprotection of the side chain functions were achieved by treatment with reagent K or slight modifications of it. Alternatively, in the synthesis of those peptides, with an amidated carboxyl terminus, the fully assembled peptide was cleaved with a mixture of 90% trifluoroacetic acid, 5% ethanedithiol, and 5% water, initially at 4° C., and gradually increasing to room temperature. The deprotected peptides were precipitated with diethyl ether. In all cases, purification was by preparative, reverse-phase, high performance liquid chromatography on a $C_{18}$ bonded silica gel column with a gradient of acetonitrile/water in 0.1% trifluoroacetic acid. The homogeneous peptides were characterized by Fast Atom Bombardment mass spectrometry or electrospray mass spectrometry and amino acid analysis when applicable.

EXAMPLE 2

Bioassays

Bioactivity of synthetic peptides and MBP-peptide fusions is measured using a Cytosensor microphysiometer (Molecular Devices) to record the metabolic response of TF-1 cells (a human leukemia cell line) to IL-5 in the presence or absence of peptide. After overnight incubation without IL-5, these cells exhibited a robust increase in metabolic activity when IL-5 is added to the medium. This increase was measured by the microphysiometer as an increase in the rate of acidification of weakly buffered tissue culture medium.

TF-1 cells were seeded into microphysiometer chambers at a density of $1.5 \times 10^5$ cells/chamber and grown overnight in DMEM tissue culture medium containing 10% fetal bovine serum, but lacking the 1 ng/ml IL-5 (R&D Systems) that is required for long-term maintenance of these cells in culture. The chambers were then placed in the microphysiometer and incubated with weakly buffered DMEM/F12 medium containing 1% human serum albumin until a baseline rate of medium acidification was established. Varying dilutions of test peptide were then introduced for 15 min. None of the peptides tested had any effect on the baseline acidification rate. IL-5 at 10 ng/ml was then introduced for 25 minutes in the continued presence of test peptide. The chambers were then flushed with fresh medium.

Typically, maximal response to IL-5 occurred within 20 min. of the onset of IL-5 addition to the medium. In the absence of test peptide this response was typically a 1.5 to 2-fold increase in the rate of medium acidification. All peptides tested were able to reduce or completely block the response of the TF-1 cells to IL-5. Other, randomly chosen control peptides, at the same or higher concentrations, had no effect. The test peptides also had no effect on the robust microphysiometer response of TF-1 cells to TNFα, indicating that the test peptides were exhibiting their effect by specifically antagonizing IL-5 action. The $IC_{50}$ for test peptides was defined as that peptide concentration which gave a 50% reduction in the maximal IL-5 response when compared to the response to IL-5 alone.

EXAMPLE 3

Binding Affinity

Binding affinities of synthetic peptides for IL-5Rα were measured in a competition binding assay using radio-iodinated IL-5. Immulon 4 (Dynatech) microtiter wells were coated with streptavidin (Sigma) by incubating 100 μl of a 50 μg/ml solution in PBS for 30 min. at 37°. The wells were blocked with 200 μl of 1% BSA in PBS for 15 min. at 37°, followed by 100 μl of biotinylated mAb 179 at 5 μg/ml in PBS. Soluble IL-5Rα was then immobilized in the wells by incubating 100 μl of a solution of soluble receptor harvest diluted 1:5000 in PBS/0.1% BSA for 1 hr. at 4°. After washing away unbound receptor, 50 μl of various concentrations of test peptide diluted in PBS/0.1% BSA were added to the wells, followed by 50 μl of a fixed concentration of [$^{125}$I] IL-5 (Amersham). The binding reactions were incubated at 4° C. for 2 hr., then washed with PBS to remove unbound [$^{125}$I] IL-5. Bound [$^{125}$I] IL-5 was determined by g counting. Total binding was defined by the amount of [$^{125}$I] IL-5 bound in the absence of any competitor. Non-specific binding was defined by the amount of [$^{125}$I] IL-5 bound in the presence of 30 nM IL-5. Peptide binding data was analyzed to determine the peptide concentration required to reduce specific [$^{125}$I] IL-5 binding by 50% ($IC_{50}$). Under the conditions described the $IC_{50}$ values determined should be similar to the dissociation constant ($K_d$) of the peptides for IL-5Rα.

EXAMPLE 4

"Peptides on Plasmids"

The pJS142 vector is used for library construction and is shown in FIG. 1. Three oligonucleotide sequences are needed for library construction: ON-829 (5' ACC ACC TCC GG); ON-830 (5' TTA CTT AGT TA (SEQ ID NO:55)) and a library specific oligonucleotide of interest (5' GA GGT GGT {NNK}$_n$ TAA CTA AGT AAA GC), where {NNK}$_n$ denotes a random region of the desired length and sequence. The oligonucleotides can be 5' phosphorylated chemically during synthesis or after purification with polynucleotide kinase. They are then annealed at a 1:1:1 molar ratio and ligated to the vector.

The strain of E. coli which is preferably used for panning has the genotype: Δ(srl-recA) endA1 nupG lon-11 sulA1 hsdR17 Δ(ompT-fepC)266 ΔclpA319::kan ΔlacI lac ZU118 which can be prepared from an E. coli strain from the E. coli Genetic Stock Center at Yale University (E. coli b/r, stock center designation CGSC:6573) with genotype lon-11 sulA1. The above *E. coli* strain is prepared for use in electroporation as described by Dower et al. (1988) *Nucleic Acids Res.* 16:6127, except that 10% glycerol is used for all wash steps. The cells are tested for efficiency using 1 pg of a Bluescript plasmid (Stratagene). These cells are used for growth of the original library and for amplification of the enriched population after each round of panning.

Peptides on plasmids are released from cells for panning by gentle enzymatic digestion of the cell wall using lysozyme. After pelleting of the cell debris, the crude lysate can be used directly on most receptors. If some additional purification of the plasmid complexes is needed, a gel filtration column can be used to remove many of the low molecular weight contaminants in the crude lysate.

Panning is carried out in a buffer (HEKL) of a lower salt concentration than most physiological buffers. The panning can be conducted in microtiter wells with a receptor immobilized on a nonblocking monoclonal antibody (MAb) or by panning on beads or on columns. More specifically, in the first round of panning, 24 wells, each coated with receptor, can be used. For the second round, six wells coated with receptor (PAN sample) and 6 wells without receptor (NC sample) are typically used. Comparison of the number of plasmids in these two samples can give an indication of whether receptor specific clones are being enriched by panning. "Enrichment" is defined as the ratio of PAN transformants to those recovered from the NC sample. Enrichment of 10 fold is usually an indication that receptor specific clones are present.

In later rounds of panning, it is useful to reduce the input of lysate into the wells to lower nonspecific background binding of the plasmid complexes. In round 2, usually 100 ml of lysate per well is used. In round 3, 100 ml of lysate per well diluted with 1/10 in HEKL/BSA is used. For further rounds of panning, typically an input of plasmid transforming units of at least 1000 fold above the estimated remaining diversity is used.

The binding properties of the peptides encoded by individual clones are typically examined after 3, 4, or 5 rounds of panning, depending on the enrichment numbers observed. Typically, an ELISA that detects receptor specific binding by LacI-peptide fusion proteins is used. LacI is normally a tetramer and the minimum functional DNA binding species is a dimer. The peptides are thus displayed multivalently on the fusion protein. Assuming that a sufficient density of receptor can be immobilized in wells, the peptides fused to LacI will bind to the surface in a cooperative, multivalent fashion. This cooperative binding permits the detection of binding events of low intrinsic affinity. The sensitivity of this assay is an advantage in that initial hits of low affinity can be easily identified, but is a disadvantage in that the signal in the ELISA is not correlated with the intrinsic affinity of the peptides. Fusion of the peptides to maltose binding protein (MBP) as described below permits testing in an ELISA format where signal strength is better correlated with affinity. See FIG. 2.

DNA from clones of interest can be prepared in double stranded form using any standard miniprep procedure. The coding sequences of interesting single clones or populations of clones can be transferred to vectors that fuse those sequences in frame with the gene encoding MBP, a protein that generally occurs as a monomer in solution. The cloning of a library into pJS142 creates a BspEI restriction site near the beginning of the random coding region of the library. Digestion with BspEI and ScaI allows the purification of a ~900 bp DNA fragment that can be subcloned into one of two vectors, pELM3 (cytoplasmic) or pELM15 (periplasmic), which are simple modifications of the pMALc2 and pMALp2 vectors, respectively, available commercially from New England Biolabs. See FIGS. 2A–B. Digestion of pELM3 and pELM15 with AgeI and ScaI allows efficient cloning of the BspEI-ScaI fragment from the pJS142 library. The BspEI and AgeI ends are compatible for ligation. In addition, correct ligation of the ScaI sites is essential to recreate a functional bla (Amp resistance) gene, thus lowering the level of background clones from undesired ligation events. Expression of the tac promoter-driven MBP-peptide fusions can then be induced with IPTG.

Lysates for the LacI or MBP ELISAs are prepared from individual clones by lysing cells using lysozyme and removing insoluble cell debris by centrifugation. The lysates are then added to wells containing immobilized receptor and to control wells without receptor. Binding by the LacI or MBP peptide fusions is detected by incubation with a rabbit polyclonal antiserum directed against either LacI or MBP followed by incubation with alkaline phosphatase labeled goat anti rabbit second antibody. The bound alkaline phosphatase is detected with p-nitrophenyl phosphate chromagenic substrate.

EXAMPLE 5

"Headpiece Dimer" System

A variant of the LacI peptides-on-plasmids technique utilizes a DNA binding protein called "headpiece dimer". DNA binding by the *E. coli* lac repressor is mediated by the approximately 60 amino acid "headpiece" domain. The dimer of the headpiece domains that binds to the lac operator is normally formed by association of the much larger approximately 300 amino acid C-terminal domain. The "headpiece dimer" system utilizes headpiece dimer molecules containing two headpieces connected via short peptide linker. These proteins bind DNA with sufficient stability to allow association of a peptide epitope displayed at the C-terminus of the headpiece dimer with the plasmid encoding that peptide.

The random peptides are fused to the C-terminus of the headpiece dimer, which binds to the plasmid that encoded it to make a peptide-headpiece dimer-plasmid complex that can be screened by panning. The headpiece dimer peptides-on-plasmids system allows greater selectivity for high affinity ligands than the LacI system. Thus, the headpiece dimer system is useful for making mutagenesis libraries based on initial low-affinity hits, and selecting higher affinity variants of those initial sequences.

Figure 3A:
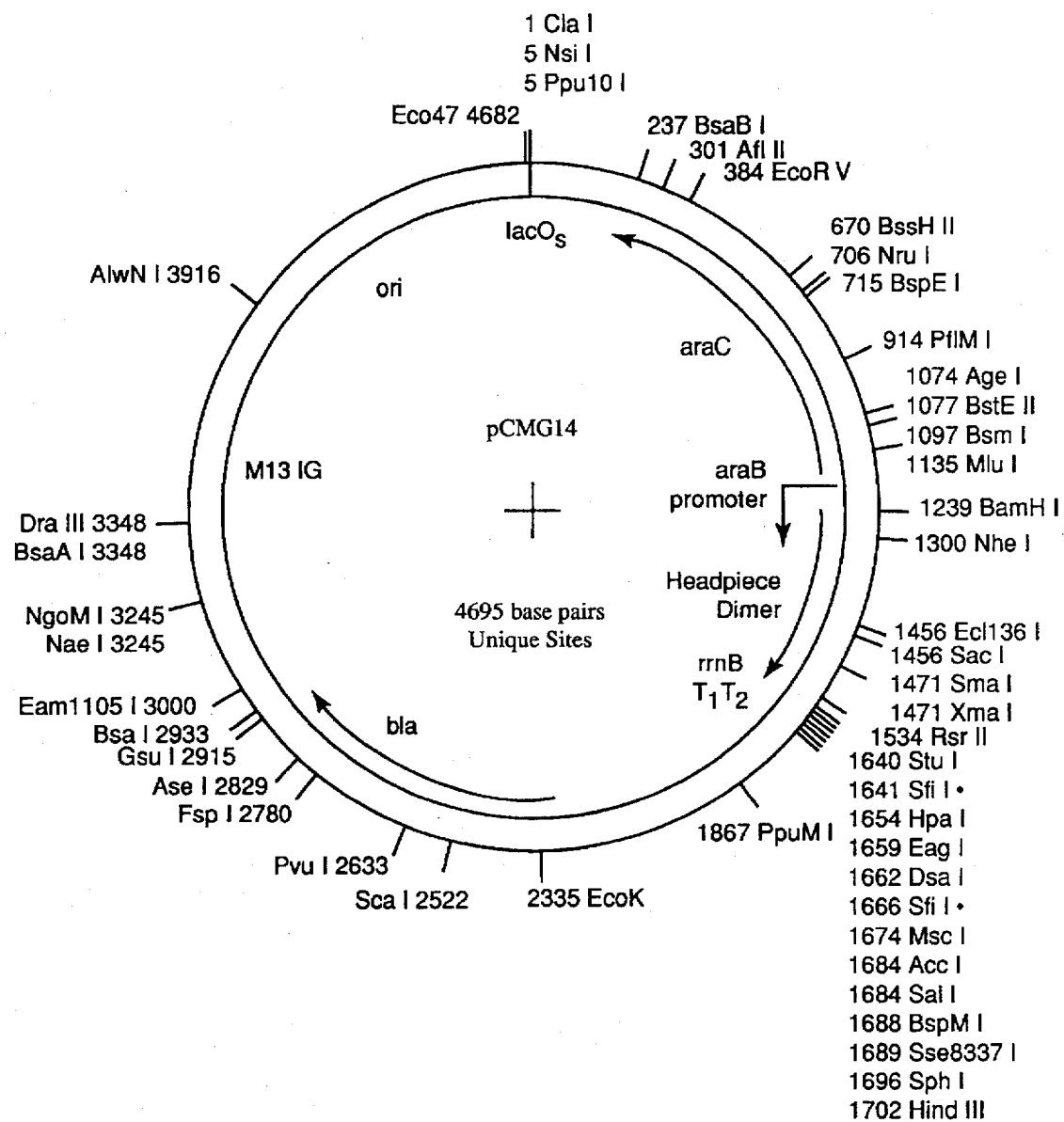
FIG. 3A depicts a restriction map and position of the genes for the construction of headpiece dimer libraries in vector pCMG14. The library plasmid includes: the rrnB transcriptional terminator, the bla gene to permit selection on ampicillin, the M13 phage intragenic region (M13 IG) to permit rescue of single-stranded DNA, a plasmid replication origin (ori), one $lacO_s$ ssequence, and the araC gene to permit positive and negative regulation of the araB promoter driving expression of the headpiece dimer fusion gene.

The libraries are constructed as with peptides on plasmids using headpiece dimer vector pCMG14 (see FIG. 3). The presence of the lac operator is not required for plasmid binding by the headpiece dimer protein. The libraries were introduced into bacterial strain comprising *E. coli* (lon-11 sulA1 hsdR17 (ompT-fepC) ΔclpA319::kan ΔlacI lac ZU118 Δ(srl-recA) 306::Tn10 and amplified under conditions of basal (A) promoter induction. Panning of headpiece dimer libraries is carried out by similar procedures to those used for LacI libraries, except that HEK buffer is used instead of HEKL buffer and elution of plasmids from the wells is performed with aqueous phenol instead of with IPTG. Sequences from headpiece dimer panning are often characterized after transfer to the MBP vector so that they can be tested in the affinity sensitive MBP ELISA and also so that populations of clones can be screened by colony lifts with labeled receptor.

The disclosures in this application of all articles and references, including patent documents, are incorporated herein by reference.

We claim:

1. A method for treating a patient suffering from a disorder that is mediated by IL-5, comprising administering to the patient, a therapeutically effective dose of a compound comprising:

(1) a core sequence of amino acids:

$$C\ X_1\ X_2\ W\ X_3\ R\ C\ X_4\ X_5\ C$$

where $X_1$ is G, I, V, or Y; $X_2$ is D or E; $X_3$ is A or V; $X_4$ is Q or P; and $X_5$ is A, E, K, M, N, S, or T (SEQ ID NO:1), and dimers and oligomers thereof, having (a) a molecular weight of less than about 5000 daltons, and (b) a binding affinity to IL5-R as expressed by an $IC_{50}$ of no more than about 100 μm, wherein from zero to all of the —C(O)NH— linkages of the peptide have been replaced by a linkage selected from the group consisting of a —CH$_2$OC(O)NR— linkage; a phosphonate linkage; a —CH$_2$S(O)$_2$NR— linkage; a —CH$_2$NR— linkage; and a —C(O)NR$^6$— linkage; and a —NHC(O)NH— linkage where R is hydrogen or lower alkyl and R$^6$ is lower alkyl, further wherein the N-terminus of said peptide or peptide mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl—NH— group; and a benzyloxycarbonyl—NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, or physiologically acceptable salts thereof.

2. A method for treating a patient suffering from a disorder that involves the production and accumulation of eosinophils in tissues, comprising administering to the patient, a therapeutically effective dose of a compound comprising:

(1) a core sequence of amino acids:

$$C\ X_1\ X_2\ W\ X_3\ R\ C\ X_4\ X_5\ C$$

where $X_1$ is G, I, V, or Y; $X_2$ is D or E; $X_3$ is A or V; $X_4$ is Q or P; and $X_5$ is A, E, K, M, N, S, or T (SEQ ID NO:1), and dimers and oligomers thereof, having (a) a molecular weight of less than about 5000 daltons, and (b) a binding affinity to IL5-R as expressed by an $IC_{50}$ of no more than about 100 μm, wherein from zero to all of the —C(O)NH— linkages of the peptide have been replaced by a linkage selected from the group consisting of a —CH$_2$OC(O)NR— linkage; a phosphonate linkage; a —CH$_2$S(O)$_2$NR— linkage; a —CH$_2$NR— linkage; and a —C(O)NR$^6$— linkage; and a —NHC(O)NH— linkage where R is hydrogen or lower alkyl and R$^6$ is lower alkyl, further wherein the N-terminus of said peptide or peptide mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl—NH— group; and a benzyloxycarbonyl—NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, or physiologically acceptable salts thereof.

3. The method of claim 1 or 2, wherein the disorder is asthma.

4. A method for treating an disorder of mediated by IL-5 the respiratory tract, said method comprising administering to a patient an inhalant composition comprising a therapeutically effective dose or amount of a compound in an aerosolized pharmaceutically acceptable carrier solution or dry powder, wherein said compound comprises:

(1) a core sequence of amino acids:

$$C\ X_1\ X_2\ W\ X_3\ R\ C\ X_4\ X_5\ C$$

where $X_1$ is G, I, V, or Y; $X_2$ is D or E; $X_3$ is A or V; X4 is Q or P; and $X_5$ is A, E, K, M, N, S, or T (SEQ ID NO:1), and dimers and oligomers thereof, having (a) a molecular weight of less than about 5000 daltons, and (b) a binding affinity to IL5-R as expressed by an $IC_{50}$ of no more than about 100 μm, wherein from zero to all of the —C(O)NH— linkages of the peptide have been replaced by a linkage selected from the group consisting of a —CH$_2$OC(O)NR— linkage; a phosphonate linkage; a —CH$_2$S(O)$_2$NR— linkage; a —CH$_2$NR— linkage; and a —C(O)NR$^6$— linkage; and a —NHC(O)NH— linkage where R is hydrogen or lower alkyl and R$^6$ is lower alkyl, further wherein the N-terminus of said peptide or peptide mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl—NH— group; and a benzyloxycarbonyl—NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, or physiologically acceptable salts thereof.

5. The method of claim 1, 2, or 4, wherein the compound administered to the patient comprises a sequence of amino acids:

C X$_1$ X$_2$ W X$_3$ R C X$_4$ X$_5$ C where X$_1$ is V; X$_2$ is E; X$_3$ is A; and X$_4$ is P (SEQ ID NO:2).

6. The method of claim 5, wherein the compound administered to the patient comprises either a sequence of amino acids:

X$_6$ X$_7$ X$_8$ V C X$_1$ X$_2$ W X$_3$ R C X$_4$ X$_5$ C where X$_6$ is D, E, G, I, M, N, P, Q, S, V, or Y; X$_7$ is G, V, or Y; and X$_8$ is F, W, or Y (SEQ ID NO:3); or a sequence of amino acids:

C X$_1$ X$_2$ W X$_3$ R C X$_4$ X$_5$ C X$_9$ where X$_9$ is E, I, K, L, M, Q, R, T, V, or Y (SEQ ID NO:4).

7. The method of claim 6, wherein the compound administered to the patient comprises a sequence of amino acids:

[X$_6$ X$_7$ X$_8$ X$_9$ C X$_1$ X$_2$ W X$_3$ R C X$_4$ X$_5$ C X$_{10}$]X$_6$ X$_7$ X$_8$ V C X$_1$ X$_2$ W X$_3$ R C X$_4$ X$_5$ C X$_9$ (SEQ ID NO:65).

8. The method of claim 7, wherein X$_6$ is D, E, G, N, P, or Q; X$_7$ is G; and X$_{10}$ is K, L, Q, R, or T (SEQ ID NO:5).

9. The method of claim 8, wherein X$_6$ is D, N, or P; X$_8$ is F or Y; and X$_{10}$ is K, R, or T (SEQ ID NO:6).

10. The method of claim 9, wherein the compound administered to the patient is selected from the group consisting of: D G Y V C V E W A R C P T C K (SEQ ID NO:7); D G Y V C V E W A R C P M C T (SEQ ID NO:8); and D G F V C V E W A R C P N C R (SEQ ID NO:9).

11. The method of claim 1, 2, or 4, wherein the compound is administered in conjunction with a β-adrenergic agonist compound.

12. The method of claim 11 wherein said b—adrenergic agonist compound is selected from the group consisting of albuterol, terbutaline, formoterol, fenoterol, and prenaline.

13. The method of claim 1, 2, or 4, wherein the compound is administered in conjunction with an antiinflammatory corticosteroid.

14. The method of claim 13 wherein said antiinflammatory corticosteroid is selected from the group consisting of beclomethasome, triamcinolone, flurisolide, and dexamethasone.

15. The method of claim 1, 2, or 4, wherein the compound is administered in conjunction with ipratropium bromide.

* * * * *

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(2)
( D ) OTHER INFORMATION: /note="Xaa is Gly, Ile, Val or Tyr."

( i x ) FEATURE:
( A ) NAME/KEY: Region
( B ) LOCATION: one-of(3)
( D ) OTHER INFORMATION: /note="Xaa is Asp or Glu."

( i x ) FEATURE:
( A ) NAME/KEY: Region
( B ) LOCATION: one-of(5)
( D ) OTHER INFORMATION: /note="Xaa is Ala or Val."

( i x ) FEATURE:
( A ) NAME/KEY: Region
( B ) LOCATION: one-of(8)
( D ) OTHER INFORMATION: /note="Xaa is Gln or Pro."

( i x ) FEATURE:
( A ) NAME/KEY: Region
( B ) LOCATION: one-of(9)
( D ) OTHER INFORMATION: /note="Xaa is Ala, Glu, Lys, Met, Asn, Ser or Thr."

( x i ) SEQUENCE DESCRIPTION: SEQ ID NO:1:

Cys Xaa Xaa Trp Xaa Arg Cys Xaa Xaa Cys
1               5                   10

( 2 ) INFORMATION FOR SEQ ID NO:2:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(9)
( D ) OTHER INFORMATION: /note="Xaa is Ala, Glu, Lys, Met, Asn, Ser or Thr."

( x i ) SEQUENCE DESCRIPTION: SEQ ID NO:2:

Cys Val Glu Trp Ala Arg Cys Pro Xaa Cys
1               5                   10

( 2 ) INFORMATION FOR SEQ ID NO:3:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(1)
    ( D ) OTHER INFORMATION: /note="Xaa is Asp, Glu, Gly, Ile, Met, Asn, Pro, Gln, Ser, Val or Tyr."

( i x ) FEATURE:
    ( A ) NAME/KEY: Region
    ( B ) LOCATION: one-of(2)
    ( D ) OTHER INFORMATION: /note="Xaa is Gly, Val or Tyr."

( i x ) FEATURE:
    ( A ) NAME/KEY: Region
    ( B ) LOCATION: one-of(3)
    ( D ) OTHER INFORMATION: /note="Xaa is Phe, Trp or Tyr."

( i x ) FEATURE:
    ( A ) NAME/KEY: Region
    ( B ) LOCATION: one-of(13)
    ( D ) OTHER INFORMATION: /note="Xaa is Ala, Glu, Lys, Met, Asn, Ser or Thr."

( x i ) SEQUENCE DESCRIPTION: SEQ ID NO:3:

Xaa  Xaa  Xaa  Val  Cys  Val  Glu  Trp  Ala  Arg  Cys  Pro  Xaa  Cys
 1              5                        10

( 2 ) INFORMATION FOR SEQ ID NO:4:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(9)
    ( D ) OTHER INFORMATION: /note="Xaa is Ala, Glu, Lys, Met, Asn, Ser or Thr."

( i x ) FEATURE:
    ( A ) NAME/KEY: Region
    ( B ) LOCATION: one-of(11)
    ( D ) OTHER INFORMATION: /note="Xaa is Glu, Ile, Lys, Leu, Met, Gln, Arg, Thr, Val or Tyr."

( x i ) SEQUENCE DESCRIPTION: SEQ ID NO:4:

Cys  Val  Glu  Trp  Ala  Arg  Cys  Pro  Xaa  Cys  Xaa
 1              5                        10

( 2 ) INFORMATION FOR SEQ ID NO:5:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region (B) LOCATION: one-of(1)
(D) OTHER INFORMATION: /note="Xaa is Asp, Glu, Gly, Asn, Pro or Gln."

(ix) FEATURE:
(A) NAME/KEY: Region
(B) LOCATION: one-of(2)
(D) OTHER INFORMATION: /note="Xaa is Gly, Val or Tyr."

(ix) FEATURE:
(A) NAME/KEY: Region
(B) LOCATION: one-of(3)
(D) OTHER INFORMATION: /note="Xaa is Phe, Trp or Tyr."

(ix) FEATURE:
(A) NAME/KEY: Region
(B) LOCATION: one-of(4)
(D) OTHER INFORMATION: /note="Xaa is Glu, Ile, Lys, Leu, Met, Gln, Arg, Thr, Val or Tyr."

(ix) FEATURE:
(A) NAME/KEY: Region
(B) LOCATION: one-of(13)
(D) OTHER INFORMATION: /note="Xaa is Ala, Glu, Lys, Met, Asn, Ser or Thr."

(ix) FEATURE:
(A) NAME/KEY: Region
(B) LOCATION: one-of(15)
(D) OTHER INFORMATION: /note="Xaa is Lys, Leu, Gln, Arg or Thr."

(xi) SEQUENCE DESCRIPTION: SEQ ID NO:5:

Xaa Gly Xaa Xaa Cys Val Glu Trp Ala Arg Cys Pro Xaa Cys Xaa
1               5                   10                  15

(2) INFORMATION FOR SEQ ID NO:6:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(1)
(D) OTHER INFORMATION: /note="Xaa is Asp, Asn or Pro."

(ix) FEATURE:
(A) NAME/KEY: Region
(B) LOCATION: one-of(2)
(D) OTHER INFORMATION: /note="Xaa is Gly, Val or Tyr."

(ix) FEATURE:
(A) NAME/KEY: Region
(B) LOCATION: one-of(3)
(D) OTHER INFORMATION: /note="Xaa is Phe or Tyr."

(ix) FEATURE:
(A) NAME/KEY: Region
(B) LOCATION: one-of(4)
(D) OTHER INFORMATION: /note="Xaa is Glu, Ile, Lys, Leu, Met, Gln, Arg, Thr, Val or Tyr."

(ix) FEATURE:
(A) NAME/KEY: Region
(B) LOCATION: one-of(7)
(D) OTHER INFORMATION: /note="Xaa is Asp or Glu."

(ix) FEATURE:
(A) NAME/KEY: Region
(B) LOCATION: one-of(9)
(D) OTHER INFORMATION: /note="Xaa is Ala or Val."

(ix) FEATURE:

( A ) NAME/KEY: Region
            ( B ) LOCATION: one-of(12)
            ( D ) OTHER INFORMATION: /note="Xaa is Gln or Pro."

( i x ) FEATURE:
            ( A ) NAME/KEY: Region
            ( B ) LOCATION: one-of(13)
            ( D ) OTHER INFORMATION: /note="Xaa is Ala, Glu, Lys, Met, Asn,
                Ser or Thr."

( i x ) FEATURE:
            ( A ) NAME/KEY: Region
            ( B ) LOCATION: one-of(15)
            ( D ) OTHER INFORMATION: /note="Xaa is Lys, Arg or Thr."

( x i ) SEQUENCE DESCRIPTION: SEQ ID NO:6:

Xaa  Gly  Xaa  Xaa  Cys  Xaa  Xaa  Trp  Xaa  Arg  Cys  Xaa  Xaa  Cys  Xaa
1                  5                            10                           15

( 2 ) INFORMATION FOR SEQ ID NO:7:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:7:

Asp  Gly  Tyr  Val  Cys  Val  Glu  Trp  Ala  Arg  Cys  Pro  Thr  Cys  Lys
1                  5                            10                           15

( 2 ) INFORMATION FOR SEQ ID NO:8:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:8:

Asp  Gly  Tyr  Val  Cys  Val  Glu  Trp  Ala  Arg  Cys  Pro  Met  Cys  Thr
1                  5                            10                           15

( 2 ) INFORMATION FOR SEQ ID NO:9:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:9:

Asp  Gly  Phe  Val  Cys  Val  Glu  Trp  Ala  Arg  Cys  Pro  Asn  Cys  Arg
1                  5                            10                           15

( 2 ) INFORMATION FOR SEQ ID NO:10:

( i ) SEQUENCE CHARACTERISTICS:
            ( A ) LENGTH: 29 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:10:

```
Gly Gly Cys Xaa Xaa Xaa Xaa Xaa Xaa Xaa Xaa Xaa Xaa Cys Gly Gly
 1               5                          10                         15
Gly Gly Ser Gly Gly Gly Gly Ser Gly Gly Gly Gly Ser
             20                  25
```

( 2 ) INFORMATION FOR SEQ ID NO:11:

( i ) SEQUENCE CHARACTERISTICS:
  ( A ) LENGTH: 31 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:11:

```
Gly Gly Cys Xaa Xaa Xaa Xaa Xaa Xaa Xaa Xaa Xaa Xaa Xaa Xaa Cys
 1               5                          10                         15
Gly Gly Gly Gly Ser Gly Gly Gly Gly Ser Gly Gly Gly Gly Ser
             20                  25                      30
```

( 2 ) INFORMATION FOR SEQ ID NO:12:

( i ) SEQUENCE CHARACTERISTICS:
  ( A ) LENGTH: 28 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:12:

```
Xaa Xaa Xaa Cys Xaa Xaa Xaa Xaa Xaa Cys Xaa Xaa Xaa Gly Gly Gly
 1               5                          10                         15
Gly Ser Gly Gly Gly Gly Ser Gly Gly Gly Gly Ser
             20                  25
```

( 2 ) INFORMATION FOR SEQ ID NO:13:

( i ) SEQUENCE CHARACTERISTICS:
  ( A ) LENGTH: 29 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:13:

```
Xaa Xaa Xaa Cys Xaa Xaa Xaa Xaa Xaa Xaa Cys Xaa Xaa Xaa Gly Gly
 1               5                          10                         15
Gly Gly Ser Gly Gly Gly Gly Ser Gly Gly Gly Gly Ser
             20                  25
```

( 2 ) INFORMATION FOR SEQ ID NO:14:

( i ) SEQUENCE CHARACTERISTICS:
  ( A ) LENGTH: 30 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:14:

```
Xaa Xaa Xaa Cys Xaa Xaa Xaa Xaa Xaa Xaa Xaa Cys Xaa Xaa Xaa Gly
 1               5                          10                         15
```

```
        Gly  Gly  Gly  Ser  Gly  Gly  Gly  Gly  Ser  Gly  Gly  Gly  Gly  Ser
                   20                      25                          30
```

( 2 ) INFORMATION FOR SEQ ID NO:15:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Xaa  Xaa  Xaa  Cys  Xaa  Xaa  Xaa  Xaa  Xaa  Xaa  Xaa  Xaa  Cys  Xaa  Xaa  Xaa
1                 5                           10                          15

Gly  Gly  Gly  Gly  Ser  Gly  Gly  Gly  Gly  Ser  Gly  Gly  Gly  Gly  Ser
              20                        25                          30
```

( 2 ) INFORMATION FOR SEQ ID NO:16:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Xaa  Xaa  Xaa  Cys  Xaa  Xaa  Xaa  Xaa  Xaa  Xaa  Xaa  Xaa  Xaa  Cys  Xaa  Xaa
1                 5                           10                          15

Xaa  Gly  Gly  Gly  Gly  Ser  Gly  Gly  Gly  Gly  Ser  Gly  Gly  Gly  Gly  Ser
              20                         25                          30
```

( 2 ) INFORMATION FOR SEQ ID NO:17:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Xaa  Xaa  Xaa  Cys  Xaa  Xaa  Xaa  Xaa  Xaa  Xaa  Xaa  Xaa  Xaa  Xaa  Cys  Xaa
1                 5                           10                          15

Xaa  Xaa  Gly  Gly  Gly  Gly  Ser  Gly  Gly  Gly  Gly  Ser  Gly  Gly  Gly  Gly
              20                         25                          30

Ser
```

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Gly  Gly  Gly  Gly  Ser  Gly  Gly  Gly  Gly  Ser  Gly  Gly  Gly  Gly  Ser
1                  5                       10                          15
```

( 2 ) INFORMATION FOR SEQ ID NO:19:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:19:

```
Xaa Xaa Xaa Xaa Xaa Xaa Xaa Trp Arg Val Pro Cys Gly Gly
 1               5                  10
```

( 2 ) INFORMATION FOR SEQ ID NO:20:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

```
Gly Gly Cys Trp Ser Gly Glu Xaa Xaa Xaa Xaa Xaa Xaa Xaa
 1               5                  10
```

( 2 ) INFORMATION FOR SEQ ID NO:21:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:21:

```
Val Glu Val Cys Thr Arg Ser Val Ala Thr His Ser Trp Val Cys Gly
 1               5                  10                  15

Ile Asp
```

( 2 ) INFORMATION FOR SEQ ID NO:22:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:22:

```
Xaa Gly Tyr Val Cys Val Glu Trp Ala Arg Cys Gln Thr Cys Xaa
 1               5                  10                  15
```

( 2 ) INFORMATION FOR SEQ ID NO:23:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:23:

```
Xaa Leu Arg Gly Cys Arg Glu Arg Tyr Met Leu Cys Val Ser Asp Xaa
 1               5                  10                  15
```

( 2 ) INFORMATION FOR SEQ ID NO:24:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(5)
        ( D ) OTHER INFORMATION: /note="Xaa is Ile, Leu, Phe, Val or Met."

( i x ) FEATURE:
        ( A ) NAME/KEY: Region
        ( B ) LOCATION: one-of(6)
        ( D ) OTHER INFORMATION: /note="Xaa is Gly, Arg, Ser or Cys."

( x i ) SEQUENCE DESCRIPTION: SEQ ID NO:24:

```
Arg  Xaa  Xaa  Cys  Xaa  Xaa  Xaa  Xaa  Xaa  Xaa  Xaa  Xaa  Xaa  Xaa  Xaa  Xaa
 1                    5                             10                            15
Xaa  Xaa  Xaa
```

( 2 ) INFORMATION FOR SEQ ID NO:25:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Asp  Gly  Tyr  Val  Cys  Val  Glu  Trp  Ala  Arg  Cys  Pro  Lys  Cys  Xaa
 1                    5                             10                            15
```

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
Asp  Gly  Tyr  Val  Cys  Gly  Glu  Trp  Val  Xaa  Cys  Pro  Ser  Cys  Thr
 1                    5                             10                            15
```

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Asp  Gly  Tyr  Val  Cys  Val  Glu  Trp  Val  Arg  Cys  Pro  Thr  Cys  Arg
 1                    5                             10                            15
```

( 2 ) INFORMATION FOR SEQ ID NO:28:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:28:

Asp Gly Trp Val Cys Val Glu Trp Val Arg Cys Gln Thr Cys Tyr
1               5                   10                  15

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

Glu Gly Tyr Val Cys Val Glu Trp Ala Arg Cys Pro Ser Cys Lys
1               5                   10                  15

( 2 ) INFORMATION FOR SEQ ID NO:30:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

Glu Gly Tyr Val Cys Val Glu Trp Ala Arg Cys Pro Ser Cys Val
1               5                   10                  15

( 2 ) INFORMATION FOR SEQ ID NO:31:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

Glu Gly Trp Val Cys Val Glu Trp Ala Arg Cys Pro Thr Cys Leu
1               5                   10                  15

( 2 ) INFORMATION FOR SEQ ID NO:32:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

Gly Gly Trp Val Cys Val Asp Trp Ala Arg Cys Pro Thr Cys Leu
1               5                   10                  15

( 2 ) INFORMATION FOR SEQ ID NO:33:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:33:

Gly Gly Tyr Val Cys Val Glu Trp Ala Arg Cys Pro Ser Cys Gln
1               5                   10                  15

( 2 ) INFORMATION FOR SEQ ID NO:34:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:34:

Ile Gly Trp Val Cys Val Glu Trp Ala Arg Cys Pro Ala Cys Lys
1               5                   10                  15

( 2 ) INFORMATION FOR SEQ ID NO:35:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:35:

Met Gly Trp Val Cys Val Glu Trp Ala Arg Cys Pro Thr Cys Leu
1               5                   10                  15

( 2 ) INFORMATION FOR SEQ ID NO:36:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:36:

Asn Gly Tyr Val Cys Val Glu Trp Ala Arg Cys Pro Met Cys Lys
1               5                   10                  15

( 2 ) INFORMATION FOR SEQ ID NO:37:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:37:

Asn Gly Trp Val Cys Val Asp Trp Ala Arg Cys Pro Ser Cys Arg
1               5                   10                  15

( 2 ) INFORMATION FOR SEQ ID NO:38:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:38:

Asn Gly Tyr Val Cys Ile Glu Trp Ala Arg Cys Pro Ser Cys Arg
1               5                   10                  15

( 2 ) INFORMATION FOR SEQ ID NO:39:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:39:

Asn Gly Tyr Val Cys Val Glu Trp Ala Arg Cys Pro Ser Cys Ile
1               5                   10                  15

( 2 ) INFORMATION FOR SEQ ID NO:40:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:40:

Asn Gly Tyr Val Cys Tyr Glu Trp Ala Arg Cys Pro Met Cys Lys
1               5                   10                  15

( 2 ) INFORMATION FOR SEQ ID NO:41:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:41:

Pro Gly Tyr Val Cys Val Asp Trp Ala Arg Cys Pro Glu Cys Arg
1               5                   10                  15

( 2 ) INFORMATION FOR SEQ ID NO:42:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:42:

Gln Gly Tyr Val Cys Val Glu Trp Ala Arg Cys Pro Met Cys Thr
1               5                   10                  15

( 2 ) INFORMATION FOR SEQ ID NO:43:

( i ) SEQUENCE CHARACTERISTICS:
   ( A ) LENGTH: 15 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:43:

Gln Gly Tyr Val Cys Val Glu Trp Ala Arg Cys Pro Ser Cys Met
1               5                   10                  15

( 2 ) INFORMATION FOR SEQ ID NO:44:

( i ) SEQUENCE CHARACTERISTICS:
   ( A ) LENGTH: 15 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:44:

Ser Gly Trp Val Cys Val Glu Trp Ala Arg Cys Pro Ser Cys Ile
1               5                   10                  15

( 2 ) INFORMATION FOR SEQ ID NO:45:

( i ) SEQUENCE CHARACTERISTICS:
   ( A ) LENGTH: 15 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:45:

Val Gly Tyr Val Cys Val Glu Trp Ala Arg Cys Pro Met Cys Arg
1               5                   10                  15

( 2 ) INFORMATION FOR SEQ ID NO:46:

( i ) SEQUENCE CHARACTERISTICS:
   ( A ) LENGTH: 15 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:46:

Pro Gly Tyr Val Cys Val Asp Trp Ala Arg Cys Pro Met Cys Lys
1               5                   10                  15

( 2 ) INFORMATION FOR SEQ ID NO:47:

( i ) SEQUENCE CHARACTERISTICS:
   ( A ) LENGTH: 15 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:47:

Pro Gly Tyr Val Cys Val Asp Trp Ala Arg Cys Pro Met Cys Gln
1               5                   10                  15

( 2 ) INFORMATION FOR SEQ ID NO:48:

( i ) SEQUENCE CHARACTERISTICS:
 ( A ) LENGTH: 15 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:48:

Pro Gly Tyr Val Cys Val Asp Trp Ala Arg Cys Pro Ala Cys Lys
1               5                   10                  15

( 2 ) INFORMATION FOR SEQ ID NO:49:

( i ) SEQUENCE CHARACTERISTICS:
 ( A ) LENGTH: 15 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:49:

Pro Val Tyr Val Cys Val Asp Trp Ala Arg Cys Pro Met Cys Gln
1               5                   10                  15

( 2 ) INFORMATION FOR SEQ ID NO:50:

( i ) SEQUENCE CHARACTERISTICS:
 ( A ) LENGTH: 15 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:50:

Gln Gly Trp Val Cys Val Glu Trp Ala Arg Cys Pro Thr Cys Glu
1               5                   10                  15

( 2 ) INFORMATION FOR SEQ ID NO:51:

( i ) SEQUENCE CHARACTERISTICS:
 ( A ) LENGTH: 15 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:51:

Val Gly Tyr Val Cys Val Glu Trp Ala Arg Cys Pro Thr Cys Leu
1               5                   10                  15

( 2 ) INFORMATION FOR SEQ ID NO:52:

( i ) SEQUENCE CHARACTERISTICS:
 ( A ) LENGTH: 15 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:52:

Val Gly Tyr Val Cys Val Asp Trp Ala Arg Cys Pro Glu Cys Arg
1               5                   10                  15

( 2 ) INFORMATION FOR SEQ ID NO:53:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:53:

```
Gly Tyr Val Cys Val Glu Trp Ala Arg Cys Gln Thr Cys
1               5                   10
```

( 2 ) INFORMATION FOR SEQ ID NO:54:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:54:

ACCACCTCCG G                                                                                                     11

( 2 ) INFORMATION FOR SEQ ID NO:55:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:55:

TTACTTAGTT A                                                                                                     11

( 2 ) INFORMATION FOR SEQ ID NO:56:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
Leu Glu Ser Gly Gln Val Val His Gly Glu Gln Val Gly Gly Glu Ala
1               5                   10                  15
Ser Gly Ala Val Asn Gly Arg Gly Leu Ala Gly Gln
                20                  25
```

( 2 ) INFORMATION FOR SEQ ID NO:57:

( i ) SEQUENCE CHARACTERISTICS:
        ( A ) LENGTH: 93 base pairs
        ( B ) TYPE: nucleic acid
        ( C ) STRANDEDNESS: double
        ( D ) TOPOLOGY: linear ( i i ) MOLECULE TYPE: DNA (oligonucleotide)

( x i ) SEQUENCE DESCRIPTION: SEQ ID NO:57:

CTCGAGAGCG GGCAGGTGGT GCATGGGGAG CAGGTGGGTG GTGAGGCCTC CGGGGCCGTT    60

AACGGCCGTG GCCTAGCTGG CCAATAAGTC GAC    93

(2) INFORMATION FOR SEQ ID NO:58:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

```
Leu Glu Ser Gly Gln Val Val His Gly Glu Gln Val Gly Gly Glu Ala
 1               5                  10                  15
Ser Gly Gly Gly
            20
```

(2) INFORMATION FOR SEQ ID NO:59:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

```
Gln Thr Asn Ser Ser Ser Asn Asn Asn Asn Asn Asn Asn Asn Asn Asn
 1               5                  10                  15
Leu Gly Ile Glu Gly Arg Thr Gly His Val Ala Arg Glu Phe Gly Ser
                20                  25                  30
Ser Arg Val Asp Leu Gln Ala Ser
            35                  40
```

(2) INFORMATION FOR SEQ ID NO:60:

(i) SEQUENCE CHARACTERISTICS:
        (A) LENGTH: 122 base pairs
        (B) TYPE: nucleic acid
        (C) STRANDEDNESS: double
        (D) TOPOLOGY: linear (ii) MOLECULE TYPE: DNA (oligonucleotide)

(xi) SEQUENCE DESCRIPTION: SEQ ID NO:60:

```
CAGACTAATT CGAGCTCGAA CAACAACAAC AATAACAATA ACAACAACCT CGGGATCGAG     60
GGAAGGACCG GTCACGTGGC CCGGGAATTC GGATCCTCTA GAGTCGACCT GCAGGCAAGC    120
TT                                                                   122
```

(2) INFORMATION FOR SEQ ID NO:61:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Gly Arg Thr Gly Gly Gly
 1               5
```

(2) INFORMATION FOR SEQ ID NO:62:

(i) SEQUENCE CHARACTERISTICS:
        (A) LENGTH: 28 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:62:

```
Glu Ala Ala Met Ala Glu Leu Asn Tyr Ile Pro Arg Ser Gln Glu Ala
1               5                   10                  15

Ser Gly Ala Val Asn Gly Arg Gly Leu Ala Gly Gln
            20                  25
```

( 2 ) INFORMATION FOR SEQ ID NO:63:

( i ) SEQUENCE CHARACTERISTICS:
( A ) LENGTH: 93 base pairs
( B ) TYPE: nucleic acid
( C ) STRANDEDNESS: double
( D ) TOPOLOGY: linear ( i i ) MOLECULE TYPE: DNA (oligonucleotide)

( x i ) SEQUENCE DESCRIPTION: SEQ ID NO:63:

```
GAAGCGGCGA TGGCGGAGCT GAATTACATT CCCCGGTCGC AGGAGGCCTC CGGGGCCGTT        60

AACGGCCGTG GCCTAGCTGG CCAATAAGTC GAC                                     93
```

( 2 ) INFORMATION FOR SEQ ID NO:64:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:64:

```
Glu Ala Ala Met Ala Glu Leu Asn Tyr Ile Pro Arg Ser Gln Glu Ala
1               5                   10                  15

Ser Gly Gly Gly
            20
```

( 2 ) INFORMATION FOR SEQ ID NO:65:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(1)
( D ) OTHER INFORMATION: /note="Xaa is Asp, Glu, Gly, Ile, Met,
Asn, Pro, Gln, Ser, Val or Tyr."

( i x ) FEATURE:
( A ) NAME/KEY: Region
( B ) LOCATION: one-of(2)
( D ) OTHER INFORMATION: /note="Xaa is Gly, Val or Tyr."

( i x ) FEATURE:
( A ) NAME/KEY: Region
( B ) LOCATION: one-of(3)
( D ) OTHER INFORMATION: /note="Xaa is Phe, Trp or Tyr."

( i x ) FEATURE:
( A ) NAME/KEY: Region
( B ) LOCATION: one-of(13)

(D) OTHER INFORMATION: /note="Xaa is Ala, Glu, Lys, Met, Asn, Ser or Thr."

(ix) FEATURE:
  (A) NAME/KEY: Region
  (B) LOCATION: one-of(15)
  (D) OTHER INFORMATION: /note="Xaa is Glu, Ile, Lys, Leu, Met, Gln, Arg, Thr, Val or Tyr."

(xi) SEQUENCE DESCRIPTION: SEQ ID NO:65:

Xaa Xaa Xaa Val Cys Val Glu Trp Ala Arg Cys Pro Xaa Cys Xaa
 1           5                   10                  15